United States Patent [19]
Schilling, Jr.

[11] Patent Number: 4,614,812
[45] Date of Patent: Sep. 30, 1986

[54] NOVEL PROCESS FOR PROMOTING HYDROSILATION REACTIONS USING A SECOND HYDROSILANE

[75] Inventor: Curtis L. Schilling, Jr., Croton-on-the-Hudson, N.Y.

[73] Assignee: Union Carbide Corporation, Danbury, Conn.

[21] Appl. No.: 815,007

[22] Filed: Dec. 31, 1985

[51] Int. Cl.$^4$ .............................. C07F 7/08; C07F 7/10; C07F 7/18
[52] U.S. Cl. ................................. 556/406; 556/415; 556/420; 556/440; 556/445; 556/464
[58] Field of Search ............... 556/479, 420, 415, 445, 556/440, 406, 464

[56] References Cited

U.S. PATENT DOCUMENTS

| | | | |
|---|---|---|---|
| 2,632,013 | 10/1946 | Wagner et al. | 556/479 |
| 2,823,218 | 12/1955 | Spier et al. | 556/479 |
| 2,851,473 | 9/1958 | Wagner et al. | 556/479 |
| 3,576,027 | 7/1968 | Fish | 556/479 |
| 3,925,434 | 1/1975 | Chuang | 556/479 |
| 4,276,426 | 6/1981 | Lindner et al. | 556/479 |

OTHER PUBLICATIONS

D. L. Bailey, 137th National Meeting, American Chemical Society, Apr. 5–14, 1960.
R. A. Benkeser, et al., J. Organometallic Chem., 184, C3 (1980).
R. A. Benkeser, et al., J. Organometallic Chem. 90 1871 (1968).
V. A. Ponamarenko, et al., Izv. Akad. Nauk SSSR, Otdel Khim Nauk, 1610 (1960), Engl. trans., Bull Acad. Sci. USSR, Chem. Sci. Section 1496 (1960).
V. A. Ponamarenko, et al., Dokl. Akad. Nauk SSSR, 121, 307 (1958); Engl. trans. Proc. Acad. Sci. USSR, 121, 541 (1950).
V. A. Ponamarenko, et al., Dokl. Akad Nauk SSSR, 124, 838 (1959); Engl. trans. Proc. Acad. Sci. USSR, 124, 95 (1959).

*Primary Examiner*—Paul F. Shaver
*Attorney, Agent, or Firm*—Ronald A. Koatz

[57] ABSTRACT

In the process of preparing compounds containing silicon-carbon bonds by the hydrosilation reaction of a hydrosilyl reactant with an olefinic reactant in the presence of a soluble platinum catalyst, the improvement which comprises operating the process at a temperature below 150° C. and employing, as a reaction promoter, a hydrosilyl compound whereby said hydrosilyl reactant has a composition different from the composition of said promoter and whereby said promoter provides (i) a 20% increase in the amount of silicon-carbon compounds, or (ii) a 20% increase in reaction rate relative to an unpromoted reaction.

22 Claims, No Drawings

NOVEL PROCESS FOR PROMOTING HYDROSILATION REACTIONS USING A SECOND HYDROSILANE

BACKGROUND OF THE INVENTION

1. Field of the Invention

This invention relates to novel processes for improving rates and yields in hydrosilation reactions, those being addition reactions of compounds containing hydrosilyl groups, i.e., ≡SiH groups, to unsaturated compounds to form carbon-functional silicon compounds. In particular, the present invention relates to the use of a hydrosilyl compound as a promoter in these hydrosilation reactions.

2. Prior Art

The hydrosilation reaction was discovered in 1947 and is now one of the best known and most widely practiced reactions in organosilicon chemistry, including use in a wide variety of large scale commercial applications. This reaction has been the subject of several extensive reviews. 1 C. Earborn & R. W. Bott, Organometallic Compounds of the Group IV Elements (1968); E. Lukevics & M. G. Voronkov, Organic Insertion Reactions of Group IV Elements (1966).

A number of patents in the art have shown that platinum compounds can have important catalytic effects in these reactions.

U.S. Pat. No. 2,632,013 to Wagner et al, for example, is an early patent showing that various forms or compounds of platinum can be effective catalysts for hydrosilation reactions. U.S. Pat. No. 2,823,218 to Speier showed that chloroplatinic acid, a soluble form of platinum, was a particularly effective catalyst. A variety of additives to or derivatives of chloroplatinic acid have been claimed as offering some advantage over chloroplatinic acid, $H_2PtCl_6$. None of these patents teaches the use of a second hydrosilyl compound used in combination with the soluble platinum catalyst to promote the rate or yields of the first reaction.

Of the many hydrosilation reactions taught in the prior art, very few involve the hydrosilation reactions between two different hydrosilyl compounds and one unsaturated compound. Moreover, that art which does discuss this area focuses on the competitive reactivity order of the hydrosilyl compounds with regard to the unsaturated compound. That is, the art teaches which of the two hydrosilyl compounds reacts better with a third unsaturated one; there is no teaching of the positive effect one such hydrosilyl compound might have on the other in increasing the yield of the hydrosilation reaction product, i.e., the product of the reaction between the hydrosilyl reactant and the unsaturated compound, or in decreasing the reaction time in the formation of such product.

For example, work by Bailey, D. L. Bailey, remarks at the 137th National Meeting of the American Chemical Society (Apr. 5-14, 1960), and by Benkeser, R. A. Benkeser, remarks at the 165th National Meeting of the American Chemical Society (Apr. 8-13, 1973), has established the competitive reactivity order $H_3SiCl > H_2SiCl_2 > Cl_3SiH$ for reactions with alkenes, this being the reverse of the reactivity order these compounds display when they are not competing with one another. The reversal occurs because the compounds, which are more reactive competitively, effectively reduce the reactivity of the other compounds, i.e., they have a negative effect on hydrosilation reactivity. The work done by Bailey did not study and did not note any promotional effects.

Other studies, have also concentrated on the competitive effect among hydrosilyl reactants. Ponomarenko et al in Izv. Akad. Nauk SSSR, Otdel. Khim. Nauk 1610 (1960); Engl. trans. in Bull. Acad. Sci. USSR, Chem. Sci. Section 1496 (1960).

In none of this prior art is there found an example of a second hydrosilyl compound having a positive effect on the reactivity of another hydrosilyl compound. This prior art always shows the two compounds in competition with one another rather than the one promoting the other in a non-competitive hydrosilation reaction.

Two Russian papers by Ponomarenko et al. do note such a positive effect, whereby $Cl_3SiH$ and $EtSiHCl_2$ increase yields of products from reactions of $Et_2MeSiH$ with allyl ethers ($CH_2=CH—CH_2OCF_2CFClH$ or $CH_2=CHCH_2OCF_2CF_2H$) using Pt/C (platinum on carbon) catalyst. In these cases, however, high temperatures (164°-198° C.) and long reaction times (3 hrs) were used. These studies also involved the use of insoluble platinum catalysts. The same workers reacted $Et_2MeSiH$ with $CH_2=CHCH_2OCF_2CF_2H$ using $H_2PtCl_6$ at lower temperature/time (25° C./30 min), but did not use a second hydrosilyl compound in the $H_2PtCl_6$-catalyzed reaction. The authors of those papers specifically commented that no promotional effects were observed in using a second hydrosilyl compound together with chloroplatinc acid in a hydrosilation reaction conducted under mild reaction temperatures.

Thus, the use of a second hydrosilyl compound and soluble platinum catalysts to promote the large rate and/or yield enhancements disclosed in the present invention under relatively mild temperatures has not been disclosed in the prior art, and is in fact contradicted by the above prior art.

There has also been some prior art in which chloroplatinic acid, $H_2PtCl_6$, has been treated with $Cl_3SiH$ or $MeSiHCl_2$ to give solutions which served as hydrosilation catalysts. Benkeser, 90 J. Am. Chem. Soc., 1871 (1968). In those studies, however, the same reactant, i.e. $Cl_3SiH$, was evaluated as both the starting reactant and the promoter. No advantage in either rate or yield was found. Similarly, in studies involving $MeSiHCl_2$, the $MeSiHCl_2$ was evaluated as both the starting reactant and promoter, and again no promotional advantages were observed. In U.S. Pat. No. 3,576,027 to Fish, a catalyst was prepared by treating $H_2PtCl_6.6H_2O$ with $Me_2SiHCl$ in a separate step, which catalyst was then isolated and used to catalyze a reaction of $MeSiHCl_2$ with 1-octene. The catalyst there was formed in a precombination step rather than being generated in situ. Additionally, large promotional effects were not observed. These tests show once more that it would be quite unexpected to find that a second hydrosilyl compound, used in a hydrosilation reaction at mild temperatures, could actually promote the rates and yields of that reaction.

Thus, there is a need in the art for a process which can be applied to hydrosilation reactions, i.e., those between hydrosilyl groups and unsaturated compounds, which process is characterized by relatively mild temperatures and relatively fast rates, by relatively inexpensive catalysts from which the active catalysts of the invention are generated in situ, and by greatly enhanced yields of carbon-functional silicon compounds formed from the hydrosilation reaction.

OBJECTS

It is thus an object of this invention to provide a process for improving the yields and rates of hydrosilation reactions under relatively mild conditions using a second hydrosilyl promoter.

It is a further object of this invention to provide such a process employing relatively inexpensive catalysts, such as soluble platinum catalysts. An even further object of the invention is to provide such a process whereby the active catalyst is generated in situ.

Another object of the invention is to provide such a process in which the reaction scale is not limited by size and may range from several grams to several thousand kilograms.

A still further object of this invention is to provide such a process where the active catalyst can be useful at sub-ambient temperatures thereby enabling the reactions to be run at ambient pressures, obviating the need for pressure-resistant equipment.

Other objects and advantages of the invention will become apparent as the description proceeds.

BRIEF SUMMARY OF THE INVENTION

In satisfaction of the foregoing objects, this invention relates to a process for greatly improving the reaction rates and yields/selectivities in hydrosilation reactions, i.e., reactions of compounds containing hydrosilyl groups with unsaturated compounds to form carbon-functional silicon compounds:

$$\equiv SiH + C=C \xrightarrow{Pt} \equiv Si\overset{|}{\underset{|}{C}}-\overset{|}{\underset{|}{C}}H$$

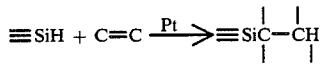

Specifically, this invention is based on the unexpected discovery that a second hydrosilyl compound promotes the hydrosilation reaction when reacted with soluble platinum compounds, e.g., chloroplatinic acid. The hydrosilyl promoter generates an active catalyst in situ, and thus no synthetic work, isolation or purification is involved in generating such catalyst as in prior art catalysts. The promoter, for example, need not be isolated by expensive ligands and is thus less expensive as well as more effective than catalysts which are bound by these ligands.

In addition, the use of the hydrosilyl promoter eliminates the induction period associated with the use of $H_2PtCl_6$ thus resulting in large rate increases in certain cases. This elimination of the induction period can also make external heating unnecessary and result in large energy savings. The hydrosilyl promoter further results in substantial improvements in product selectivity in certain hydrosilation reactions, thus increasing the commercial utility of such reactions and, in combination with the large reaction rate increases mentioned above, significantly increasing effective production capacity without building additional production facilities.

Finally, an important and novel aspect of th invention is that, in certain cases, the hydrosilyl promoter can be useful at sub-ambient temperatures. This enables some reactions to be run at ambient pressure, obviating the need for pressure-resistant equipment.

Thus the key discovery of the invention is the use of a hydrosilyl promoter in a platinum-catalyzed hydrosilation reaction which surprisingly increases catalytic effectiveness.

Although the degree to which the promotional effects may vary depending on which hydrosilyl reactant, hydrosilyl promoter, platinum compound or unsaturated olefin is selected, the invention is characterized by increases in yield or selectivity of at least 20 percent. The most striking or positive promotion effects, in terms of reaction rate and selectivity, are observed from those reactions in which the electron environment of the hydrosilyl promoter is most nearly opposite the electron environment of the hydrosilyl starting reactant. Further, strong promotional effects are observed in reactions which are normally sluggish, i.e., those which require extended heating or high catalyst levels.

DETAILED DESCRIPTION OF THE INVENTION

The present invention provides a hydrosilation process having improved rates and yields as a result of the use of a hydrosilyl promoter. This promoter reacts with a soluble platinum catalyst and a starting hydrosilyl reactant to greatly increase the yield, selectivity or rate of the hydrosilation product.

While not wishing to be bound by theory, the active catalyst is believed to be generated when platinum catalysts such as chloroplatinic acid undergo a series of reactions involving both the hydrosilyl reactant and the hydrosilyl promoter to produce a species containing Pt—Si bonds. The following is a possible representation of such reactions involving $Cl_3SiH$ and $Et_3SiH$ as the promoter and reactant, respectively. The Pt—Cl is one such group in a soluble Pt catalyst containing Pt—Cl bonds, such as $H_2PtCl_6$:

Pt—Cl + $Et_3SiH$ → $Et_3SiCl$ + Pt—H

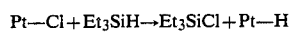

Pt—H + $Cl_3SiH$ → $H_2$ + Pt—$SiCl_3$

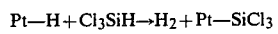

It has been reported that $Et_3SiH$ reacts with Pt—Cl bonds as shown, while $Cl_3SiH$ does not. It has also been reported that $Cl_3SiH$ reacts with Pt—H bonds to form $H_2$ and Pt—$SiCl_3$ bonds, while $Et_3SiH$ does not undergo such a reaction. It should be noted that these reactions explain the formation of Pt—Si species by established chemistry and that such species need only to be sufficiently stable in solution to act as highly efficient hydrosilation catalysts. Such species, because of their inherently high reactivity, may not be sufficiently stable to allow isolation and identification by normal chemical methods.

The catalysts for the instant invention are platinum compounds used in the form of solutions, such as solutions of $H_2PtCl_6$ (in hydrated or unhydrated form), solutions of $PtCl_4$ or $PtCl_2$, solutions of other soluble Pt compounds such as ethylene bis(platinous chloride), or Pt catalyst solutions as disclosed, for example, in U.S. Pat. No. 3,220,972. Platinum catalysts containing strongly bound stabilizing ligands such as trialkyl or triarylphosphines or acetylacetonate groups are less effective. Phosphines or other strongly bound Pt ligands appear to interfere with the mutual interaction of hydrosilyl promoter and hydrosilyl reactant with the platinum catalyst, preventing or retarding the formation of the active catalyst species of the present invention.

Because of its availability and relatively low cost (for platinum compounds), chloroplatinic acid is the preferred catalyst, although other soluble platinum compounds such as PtCl$_4$ and ethylene bis(platinous chloride) are considered equally effective.

The platinum solution is added to the reaction in a concentration range of $10^{-3}$ to $10^{-8}$ molar relative to the combined starting reactant and promoter, preferably $10^{-4}$ to $10^{-6}$ molar.

The olefinic coreactant may be any one of a variety of functional or non-functional terminally unsaturated compounds and has the general formula CH$_2$=C<. The following are examples of compounds whose hydrosilation reactions can be promoted via processes of the instant invention:

CH$_2$=CYCH$_2$Cl  CH$_2$=CYCH$_2$OR where
Y=H or R as defined below for hydrosilyl reactant
CH$_2$=CYCMe$_3$  CH$_2$=CYCH$_2$CHMe$_2$
CH$_2$=CY$\phi$  CH$_2$=CYCH$_2$OAc
CH$_2$=CYOAc  CH$_2$=CYCH$_2$O$_2$CCY=CH$_2$
CH$_2$=CYCH$_2$O$_2$CY  CH$_2$=CYO$_2$CY
CH$_2$=CHCHYCl  CH$_2$=CYCH$_2$CN Thus included are allyl and methallyl compounds, vinyl compounds, terminal alkenes, including halides, ethers, esters, nitriles, and the like, with the proviso that when the olefinic reactant is substituted to functional groups, said functional groups do not interfere with the promotion mechanism of the hydrosilation reaction. The allyl and methallyl compounds include the allyl and methallyl polyalkylene oxide ethers typical of those used commercially to prepare silicone-polyether copolymers.

The olefinic coreactant is used at 0.1–2.0 molar amounts relative to the hydrosilyl reactant, more preferably 0.5–1.5 and most preferably 0.8–1.2 molar amounts.

The hydrosilyl reactant of this invention is a silicon-bonded hydrogen reactant having the general formula R$_3$SiH where each R represents the same or different monovalent hydrocarbon group, aliphatic having 1–10 carbon atoms or aromatic having 6–20 carbon atoms free of terminal unsaturation, possibly substituted with functional groups such as halogen, cyano, carboalkoxy (ester), ether, thioether, or the like, with the proviso that when such hydrosilyl reactant is substituted with functional groups, said functional groups do not interfere with the promotion mechanism for hydrosilane-promoted hydrosilations. R may be alkyl, aryl, alkoxy, acyloxy or carbamoyloxy when R is a hydrocarbon group as defined above. Alternatively, R may be halogen, i.e., Cl$_3$SiH or siloxy.

Illustrative hydrosilyl reactants include hydrosilanes such as triethylsilane, a hydrochlorosilane such as Cl$_3$SiH, a hydrosiloxane such as (Me$_3$SiO)$_2$SiMeH, or a polyhydrosiloxane containing hydrosilyl groups at either internal or terminal positions, or both.

The following represent hydrosilyl reactants of the hydrosilane type whose hydrosilation reactions may be promoted with a hydrosilyl promoter:

| Me$_3$SiH | MeEt$_2$SiH | Me$_2$EtSiH | Et$_3$SiH |
| Pr$_3$SiH | $\phi_3$SiH | $\phi_2$MeSiH | $\phi$SiMe$_2$H |

Illustrative of the hydrosiloxanes are the following:

(Me$_3$SiO)$_2$SiMeH,  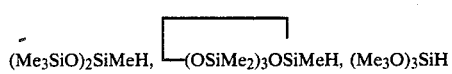(OSiMe$_2$)$_3$OSiMeH, (Me$_3$O)$_3$SiH

Me$_3$Si(OSiMe$_2$)$_x$(OSiMeH)$_y$SiMe$_3$, x = 0–300, y = 1–300
HSiMe$_2$(OSiMe$_2$)$_x$OSiMe$_2$H, MeSi[(OSiMe$_2$)$_x$OSiMe$_2$H]$_3$

HSiMe$_2$(OSiMe$_2$)$_x$(OSiMeH)$_y$OSiMe$_2$H, Me$_3$SiOSiMe$_2$H

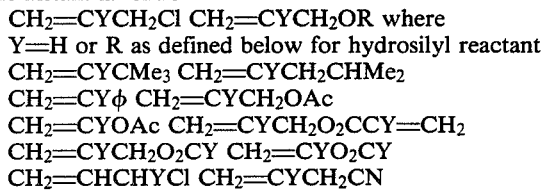(OSiMe$_2$)$_3$OSiMeOSiMe$_2$H and the like where Me groups can be replaced by functional groups free of terminal unsaturation and which do not otherwise interfere with the promotion mechanism, such as haloalkyl, cyanoalkyl, phenylalkyl, acyloxyalkyl, etc.

Other hydrosilyl reactants include halosilanes, hydroalkoxysilanes and hydroacyloxysilanes, of which the following are representative:

Cl$_3$SiH  F$_3$SiH  Br$_3$SiH  MeSiHCl$_2$
Me$_2$SiHCl  MeSiHF$_2$  Me$_2$SiFH  MeSiHBr$_2$
Me$_2$SiHBr  Me(MeO)$_2$SiH  (MeO)$_3$SiH
Me(MeCO$_2$)$_2$SiH  (EtO)$_3$SiH

In another embodiment of the invention, two R-groups taken together may form a hetero-cyclic ring including the silicon atoms, as in

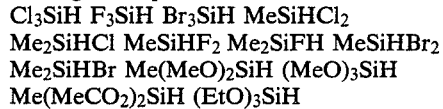, where n=3–6.

The structure of the hydrosilyl reactant may thus vary widely including but not being limited to the structures shown above, which merely exemplify some of the possibilities.

The hydrosilyl promoter may also be a hydrosilane, a hydrochlorosilane, or a hydrosiloxane exactly as defined above for the hydrosilyl reactant, with the proviso that the hydrosilyl promoter and the hydrosilyl reactant may not be the same compound when used in the same reaction. As noted above, the most effective promotion effects are observed when the hydrosilyl reactant and the hydrosilyl promoter differ substantially in structure, or in the electronic environment of the respective ≡SiH groups. Preferably, hydrosilyl promoter is selected from the group consisting of Cl$_3$SiH, MeSiHCl$_2$, Me$_2$SiHCl, Et$_3$SiH, F$_3$SiH and Br$_3$SiH.

The hydrosilyl promoter can be used in a wide range of concentrations relative to the hydrosilyl reactant or the olefinic or unsaturated coreactant. The hydrosilyl promoter is used at 0.0001–2.0 molar amounts relative to the hydrosilyl reactant, more preferably 0.0001–0.1 molar amounts. The greatest advantages from a commercial standpoint are attained when very low concentrations of hydrosilyl promoter are effective. In most cases, even with small amounts of promoter, it can simply be added to the hydrosilyl reactant and the platinum catalyst.

While the reactants, catalyst, and promoter can generally be combined in total and allowed to react, there are specific cases in which it is advantageous to vary the order of combination of either reactant, or the promoter, or combinations thereof, to obtain maximum degree of promotion. For example, promotion of the reaction between Et$_3$SiH and allyl chloride by Cl$_3$SiH appears to be optimum when a 10/1 molar mixture of allyl chloride/Cl$_3$SiH is added to Et$_3$SiH containing the chloroplatinic acid.

The reaction process of this invention may reach a reaction temperature as high as 150° C., although temperatures below 100° C. are preferred. The reaction can also be promoted at sub-ambient temperatures.

The reaction can be run under a pressurized atmosphere as high as 10 atmospheres in pressure. Alternatively, if, for example, the reaction is run at sub-ambient temperatures, the reaction can be run at ambient pressures.

Finally, the reaction may be run in time periods ranging from minutes to hours in duration, preferably 3–1000 minutes, more preferably 5–300 minutes and most preferably 10–100 minutes.

Not all reactions between hydrosilyl reactants and unsaturated compounds are promoted by all hydrosilane promoters. Within the almost infinite number of possible combinations of hydrosilane reactants, unsaturated reactants, and hydrosilane promoters, and the possible variations in reaction conditions, i.e., temperature, sequence of combination, relative concentrations, etc., under which these three components can be reacted, there will be combinations for which promotion effects are not observed. A greater element of predictability, however, can be found by controlling certain variables. The most effective promotion effects, for example, are observed when the hydrosilyl reactant and the hydrosilyl promoter differ substantially in structure, or in electronic environment of the respective $\equiv$SiH groups. For example, $Cl_3SiH$, which has strong electron attracting halogen groups, is an effective promoter for hydrosilation reactions of trialkylsilanes, such as $Et_3SiH$. Conversely, $Et_3SiH$ is an effective promoter for hydrosilation reactions of $Cl_3SiH$.

The conditions and variables for optimal promotional effect can be readily ascertained to one skilled in the art from the disclosure and examples herein. The reactions encompassed within the present invention are characterized by increases in either rate or selectivity of at least 20%.

EXAMPLES

The following specific examples and procedures are presented to illustrate the invention, but are not to be construed as limiting thereon. The examples representing this invention are numbered; those examples that are lettered are comparative examples which do not illustrate the invention. Only those examples which satisfied the requirements of 20% yield or reaction rate improvement were numbered.

Reported yields are in molar percentages and, in most examples, are given only for the desired hydrosilation product. Other by-products are obtained in many of the examples; their yields are not reported therein.

In the examples and throughout the specification, all temperatures are on the Centigrade Scale (°C.), and all percentages and parts are on a molar basis unless specified otherwise.

| | Definitions |
|---|---|
| % | percent |
| Pt | platinum |
| wt | weight |
| g | gram or grams |
| Mol-% | mole percent |
| EqM | Equimolar |
| min. or mins | minute or minutes |
| hr or hrs | hour or hours |
| sec | seconds |
| ml | milliliter |
| mm | millimeters of mercury pressure |
| Ac | —$COCH_3$ |

| | -continued |
|---|---|
| | Definitions |
| $C_6H_5$ | phenyl |
| Me | methyl |
| Et | ethyl |
| VPC | vapor phase chromatography |
| NMR | nuclear magnetic resonance |
| $D_3D'$ | heptamethylcyclotetrasiloxane: |

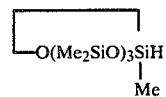

or the corresponding derivative

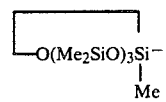

| MD'M | heptamethyltrisiloxane: |
|---|---|

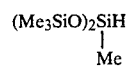

or the corresponding derivative:

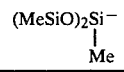

GENERAL PROCEDURE

All the reactions above were run in standard laboratory glassware of flasks of various sizes as noted in each example using magnetic stirring under nitrogen atmosphere with heat being applied by electric mantles. Flasks were also fitted with Hopkins condensers and thermometers, temperatures being recorded in Centigrade. All reaction products were identified by vapor phase chromatography (VPC) and nuclear magnetic resonance (NMR) spectroscopy. Reported yields were based on the amount of hydrosiloxane or hydrosilane charged.

SPECIFIC PROCEDURES

Comparative Example A

Reaction of $D_3D'$ with methallyl chloride; reactants combined at start.

In a 200 ml apparatus, there were combined 56.4 g (0.2 mol) of $D_3D'$, 20.0 g (0.22 mol) of methallyl chloride, and 0.2 ml of a reduced platinum catalyst (prepared according to Example 1, U.S. Pat. No. 3,220,972). Heat was applied to about 80° C. when an exothermic reaction occurred to a maximum temperature of 141° C. Reaction was complete after 1 hr., 17 mins. and was followed by cooling. The reaction mixture was suction filtered into a 100 ml flask which was fitted for vacuum distillation. The following products were isolated:

| Product | Boiling Point/ Pressure | g | Yield |
|---|---|---|---|
| $D_3D'Cl$ | 76°/17 mm (aspirator) | 17.0 | 27.0% |
| $D_3D'CH_2C(CH_3)=CH_2$ | 80°/17 mm (aspirator) | 3.0 | 4.4% |
| $D_3D'CH_2CH(CH_3)_2$ | 80°/17 mm (aspirator) | 1.6 | 2.4% |

-continued

| Product | Boiling Point/ Pressure | g | Yield |
|---|---|---|---|
| $D_3D'CH_2CH(CH_3)CH_2Cl$* | 60°/0.25 mm | 44.8 | 60.0% |
| Heavies | — | 1.2 | — |

*The yield of the desired hydrosilation product by this route was 60.0%

Comparative Example B

Reaction of equimolar mixture of $D_3D'/MD'M$ with methallyl chloride.

In a 100 apparatus, there were combined 30.5 g (0.1 mol) of 92% $D_3D'$, 22.2 g (0.1 mol) of MD'M, and 9.1 g (0.1 mol) of methallyl chloride, followed by 0.05 mol of Pt catalyst solution. Heat was applied to 100° C. over 152 min, when an exothermic reaction occurred to 130° C. Vacuum distillation of the complete reaction yielded 4.26 g (13.6%) of $M_2D'CH_2CHMeCH_2Cl$ and 21.37 g (57.4%) of $D_3D'CH_2CHMeCH_2Cl$. This example shows that neither $D_3D'$ nor MD'M is an effective promoter for reaction of the other with methallyl chloride at the equimolar level.

Comparative Example C

Reaction of $D_3D'$ with methallyl chloride; olefin added to hydrosiloxane.

In a 500 ml apparatus were placed 282 g (1.0 mol) of $D_3D'$ which was heated to 85° C., followed by addition of 0.3 ml of a solution of 4.0 wt.% of $H_2PtCl_6.6H_2O$ in 1,2-dimethoxyethane. Dropwise addition of 90.5 g (1.0 mol) of methallyl chloride was begun and continued at a rate which maintained the reaction temperature at 87°–93° C. Addition was complete in 1.5 hr., and the reaction mixture was distilled directly, yielding the following products:

| Product | Boiling Point/ Pressure | g | Yield |
|---|---|---|---|
| $D_3D'Cl$ | 77°/17 mm (aspirator) | 55.0 | 17.4% |
| $D_3D'CH_2C(CH_3)=CH_2$ | 31°/0.2 mm | trace | — |
| $D_3D'CH_2CH(CH_3)_2$ | 31°/0.2 mm | 30.5 | 9.0% |
| $D_3D'CH_2CH(CH_3)CH_2Cl$* | 55°/0.12 mm | 246.2 | 66.1% |
| Heavies | — | 11.0 | — |

*The yield of the desired hydrosilation product was 66.1%, a relative improvement of 10.2% over the 60.0% obtained in Comparative Example A.

Example 1

Reaction of equimolar mixture of $D_3D'/Cl_3SiH$ with methallyl chloride.

In a 50 ml apparatus there were combined 24.7 g (0.085 mol) of $D_3D'$, 11.4 g (0.085 mol) of $Cl_3SiH$, and 7.7 g (0.085 mol) of methallyl chloride. Pt catalyst solution (0.05 ml) was added at 20° C. causing a gentle exothermic reaction to 78° C. in 10 min. Reaction was complete in 15 min. The yield of $D_3D'CH_2CHMeCH_2Cl$ as analyzed by VPC was greater than 90%, a substantial improvement over the yields of Comparative Examples A, B and C, and a demonstration of non-competitive promotion by $Cl_3SiH$ of hydrosiloxane reactivity.

Example 2

Reaction of $D_3D'$ with methallyl chloride promoted by 9 mol-% $Cl_3SiH$.

In the apparatus of Example 3, there were combined 30.5 g of 92% $D_3D'$ (8% $D_4$, 0.1 mol of $D_3D'$), 9.1 g (0.1 mol) of methallyl chloride, and 0.5 g $Cl_3SiH$. Pt catalyst solution (0.05 ml) was added at 20° C.; after 42 min. temperature was 29° C. and 0.7 g additional $Cl_3SiH$ was added. Reaction temperature rose gradually to 107° C. over 87 min, when reaction was complete. Vacuum distillation yielded 32.85 g (88.2%) of $D_3D'CH_2CHMeCH_2Cl$, the yield being similar to that of Example 1 which employed a much larger amount of $Cl_3SiH$ promoter.

Example 3

Reaction of $D_3D'$ with methallyl chloride promoted by 11 mol-% $Cl_3SiH$ at 50° C.

The reaction of Example 2 was repeated except that 1.5 g $Cl_3SiH$ was added at the start and the reaction mixture was heated to 50° C. prior to addition of Pt catalyst. There was a rapid exothermic reaction to 148.5° C. in 7 min at which point the reaction was complete, yielding 28.49 g (76.5%) of $D_3D'CH_2CHMeCH_2Cl$ on distillation. The lower yield relative to Examples 1 and 2, and the higher amount of non-volatile products (11.5% of total) indicate little advantage to adding catalyst at the higher temperature.

Example 4

Reaction of equimolar mixture of $D_3D'/MeSiHCl_2$ with methallyl chloride.

In a 50 ml apparatus, there were combined 9.7 g (0.085 mol) of $MeSiHCl_2$, 24.2 g (0.085 mol) of $D_3D'$, and 7.8 g (0.085 mol) of methallyl chloride. Pt catalyst solution (0.05 ml) was added at 20° C. Heat was applied intermittently causing an exothermic reaction to 75° C. after 26 min. Reaction was complete after 40 min, and was vacuum distilled, yielding 23.8 g (76.1%) of $D_3D'CH_2CHMeCH_2Cl$. This example shows that $MeSiHCl_2$ is slightly less effective than $Cl_3SiH$ as a promoter for the reaction of $D_3D'$ with methallyl chloride.

Comparative Example D

Reaction of equimolar mixtures of $D_3D'/Et_3SiH$ with methallyl chloride.

In a 100 ml apparatus, there were combined 28.4 g (0.1 mol) of 98% $D_3D'$, 11.6 g (0.1 mol) of $Et_3SiH$, and 9.1 g (0.1 mol) of methallyl chloride. Pt catalyst solution (0.05 ml) was added at 21° C. Heat was applied to 99° C. over 108 min, when a later exothermic reaction to 118° C. occurred. Reaction was complete and was vacuum distilled, yielding 24.3 g (65.2%) of $D_3D'CH_2CHMeCH_2Cl$. This example shows that $Et_3SiH$ is much less effective than $Cl_3SiH$ or $MeSiHCl_2$ as a promoter for the reaction of $D_3D'$ with methallyl chloride when used at the equimolar level.

Comparative Example E

Reaction of $D_3D'$ with methallyl chloride promoted by 10 mol-% $MeSiCl_3$.

In a 50 ml apparatus, there were combined 30.5 g (0.1 mol) of 92% $D_3D'$, 9.1 g (0.1 mol) of methallyl chloride, and 1.5 g (0.01 mol) of $MeSiCl_3$. Pt catalyst solution (0.05 ml) was added at 21° C. Heat was applied to 89° C. over 41 min followed by a gentle exothermic reaction to 123.5° C. Reaction was complete in 45 min, and was vacuum distilled, yielding 26.6 g (71.4%) of $D_3D'CH_2CHMeCH_2Cl$. This example shows that $MeSiCl_3$ is not as effective as either $Cl_3SiH$ or $MeSiHCl_2$ in promoting the reaction of $D_3D'$ with methallyl chloride, although it did demonstrate a positive effect.

Comparative Example F

Reaction of equimolar mixture of $D_3D'/Me_2SiHCl$ with methallyl chloride.

In a 100 ml apparatus, there were combined 30.5 g (0.1 mol) of 92% $D_3D'$, 9.1 g (0.1 mol) of methallyl chloride, and 9.5 g (0.1 mol) of $Me_2SiHCl$. Heat was applied to 43° C. and 0.05 ml Pt catalyst solution added, causing an exothermic reaction to 95.5° C. in 26 min, with the heat source removed. Vacuum distillation of the complete reaction yielded 7.82 g (42.3%) of $Me_2SiClCH_2CHMeCH_2Cl$ and 16.89 g (45.3%) of $D_3D'CH_2CHMeCH_2Cl$. This example shows that neither $Me_2SiHCl$ nor $D_3D'$ is an effective promoter for reaction of the other with methallyl chloride when used at the equimolar level.

TABLE I

PROMOTION OF $D_3D'$ AND METHALLYL CHLORIDE

| Example | REACTANT A | OLEFIN | PROMOTER | YIELD % | TIME |
|---|---|---|---|---|---|
| Comp. A | $D_3D'$ | $CH_2=CMeCH_2Cl$ | — | 60* | 77 min |
| Comp. B | $D_3D'$ | $CH_2=CMeCH_2Cl$ | EqM. MD'M | 57.4 | 152 min |
| Comp. C | $D_3D'$ | $CH_2=CMeCH_2Cl$ | — | 66.1 | 90 min |
| 1 | $D_3D'$ | $CH_2=CMeCH_2Cl$ | EqM. $Cl_3SiH$ | >90 | 15 min |
| 2 | $D_3D'$ | $CH_2=CMeCH_2Cl$ | 9 mol % $Cl_3SiH$ | 88.2** | 87 min |
| 3 | $D_3D'$ | $CH_2=CMeCH_2Cl$ | 11 mol % $Cl_3SiH$ | 76.5 | 7 min |
| 4 | $D_3D'$ | $CH_2=CMeCH_2Cl$ | EqM. $MeSiHCl_2$ | 76.1 | 40 min |
| Comp. D | $D_3D'$ | $CH_2=CMeCH_2Cl$ | EqM. $Et_3SiH$ | 65.2 | 108 min |
| Comp. E | $D_3D'$ | $CH_2=CMeCH_2Cl$ | 10 mol % $MeSiCl_3$ | 71.4 | 45 min |
| Comp. F | $D_3D'$ | $CH_2=CMeCH_2Cl$ | EqM. $Me_2SiHCl$ | 45.3*** | 26 min |

*When Olefin was added to hydrosiloxane in dropwise manner rather than the reactants being combined at the start as in Comparative Example A, the yield was 66.1% (see Comparative Example C).
**When mixture was heated to 50° C. (versus 20° C.) prior to addition of Pt catalyst solution, yield was 76.5% indicating little advantage to adding catalyst at high temperature in this reaction (see Example 3).
***$Me_2SiHCl$ competed rather than promoted production with $D_3D'$.

This table shows that yields and rates of $D_3D'$ can be greatly improved depending on the nature and quantity of the promotor. Example 1 shows the most dramatic increase, relative to an unpromoted reaction, in both yield (greater than 30% absolute) and rate when using equimolar $Cl_3SiH$. Using a much smaller quantity of $Cl_3SiH$, i.e., equimolar versus 9 mol-%, gave substantially equivalent yields even though the rate of the reaction was not diminished (compare Example 1 to Example 2). As observed from this table, order of reactivity for greatest yield production is as follows: $Cl_3SiH > MeSiHCl_2 > MeSiCl_3 > Et_3SiH > Me_2SiHCl$.

Comparative Example G

Reaction of MD'M with methallyl chloride; reactants combined at start.

In the apparatus of Comparative Example A, there were combined 43.1 (0.194 mol) of MD'M, 19.0 g (0.21 mol) methallyl chloride, and 0.32 ml of the catalyst used in Comparative Example A. Heat was applied to 94° C. at which point the reaction mixture was refluxing. The reflux temperature increased over 2 hrs. to 143° C. The product mixture was transferred to a 100 ml flask and distilled, yielding the following products:

| Product | Boiling Point/ Pressure | g | Yield |
|---|---|---|---|
| Unreacted MD'M | 41°/17 mm (aspirator) | 5.9 | 13.7% |
| $M_2D'Cl$ | 50°/17 mm (aspirator) | 16.5 | 32.2% |
| $M_2D'CH_2C(CH_3)=CH_2$ | 56°/17 mm | 3.9 | 7.1% |

| Product | Boiling Point/ Pressure | g | Yield |
|---|---|---|---|
|  | (aspirator) |  |  |
| $M_2D'CH_2CH(CH_3)_2$ | — | nil | — |
| $M_2D'CH_2CH(CH_3)CH_2Cl$* | 36°/0.3 mm | 21.3 | 34.1% |
| Heavies | — | 2.2 |  |

*The yield of the desired hydrosilation product was 34.1%. The yields obtained compare favorably with those reported by Davis (J. Org. Chem. 38,838 (1973)) which were: $M_2D'CH_2C(CH_3)=CH_2$ (9%), and $M_2D'CH_2CH(CH_3)CH_2Cl$ (34%) wherein the reactants were combined at the start.

Comparative Example H

Reaction of MD'M with methallyl chloride; olefin added to hydrosiloxane.

In a 100 ml flask, there were placed 39.1 g (0.176 mol) of MD'M which was heated to 75°, when 0.1 ml of the catalyst used in Comparative Example A was added. Addition of 16.3 g (0.18 mol) of methyallyl chloride was begun, with reaction proceeding slowly for 30 mins., followed by an exothermic temperature rise to 119°. Reaction was complete after 1.5 hrs. from start of addition. Direct vacuum distillation yielded the following products:

| Product | Boiling Point/ Pressure | g | Yield |
|---|---|---|---|
| $M_2D'Cl$ | 50°/17 mm (aspirator) | 7.9 | 17.5% |
| $M_2D'CH_2C(CH_3)=CH_2$ | 31°/0.22 mm (aspirator) | 0.7 | 1.4% |
| $M_2D'CH_2CH(CH_3)_2$ | 31°/0.22 mm | 4.9 | 10.0% |
| $M_2D'CH_2CH(CH_3)CH_2Cl$* | 33°/0.18 mm | 27.6 | 50.2% |
| Heavies | — | 3.7 |  |

*The yield of the desired hydrosilation product was 50.2%, a relative improvement of 47.2% over the 34.1% obtained in Comparative Example C or the 34% reported by Davis.

Example 5

Reaction of equimolar mixture of $MD'M/Cl_3SiH$ with methallyl chloride.

In a 100 ml apparatus, there were combined 11.1 g (0.05 mol) of MD'M, 4.5 g (0.05 mol) of methallyl chloride, and 6.8 g (0.05 g mol) of $Cl_3SiH$. Pt catalyst solution (0.01 ml) was added at 40° C., causing a violent exothermic reaction to more than 100° C. in 1 min. Vacuum distillation of the complete reaction yielded 12.78 g (81.8%) of $M_2D'CH_2CHMeCH_2Cl$, indicating that $Cl_3SiH$ is an effective promoter for the reaction of MD'M with methallyl chloride. The yield here is significantly higher than in Comparative Examples G or H, and the reaction time much shorter. Note that MD'M and D₃D' are chemical models for polyhydrosiloxane fluids which are articles of commerce, demonstrating clearly that reactions of such fluids with methallyl chloride will also be promoted.

Example 6

Reaction of equimolar mixture of MD'M/MeSiHCl$_2$ with methallyl chloride.

In a 100 ml apparatus, there were combined 16.7 g (0.075 mol) of MD'M, 8.6 g (0.075 mol) of MeSiHCl$_2$, and 6.8 g (0.075 mol) of methallyl chloride, followed by addition of 0.01 ml Pt catalyst solution at 48° C. There was an exothermic reaction to 92° C. in 9 min, with the reaction being complete in 50 min. Vacuum distillation yielded 16.57 g (70.7%) of M$_2$D'CH$_2$CHMeCH$_2$Cl, showing that MeSiHCl$_2$ is slightly less effective than Cl$_3$SiH as a promoter for the reaction of MD'M with methallyl chloride at the equimolar level.

Example 7

Reaction of equimolar mixture MD'M/Et$_3$SiH with methallyl chloride.

In a 100 ml apparatus, there were combined 11.1 g (0.05 mol) of MD'M, 5.8 g (0.05 mol) of Et$_3$SiH, and 4.5 g (0.05 mol) of methallyl chloride, followed by addition of 0.01 ml Pt catalyst solution at 55° C. Heat was applied over 80 min to 95° C. when reaction was complete. Distillation yielded 51.3% of M$_2$D'CH$_2$CHMeCH$_2$Cl, indicating that Et$_3$SiH is not a very effective promoter for the reaction of MD'M with methallyl chloride when used at the equimolar level.

Comparative Example I

Reaction of equimolar mixture MD'M/Me$_2$SiHCl with methallyl chloride.

In a 100 ml apparatus, there were combined 22.3 g (0.1 mol) of MD'M, 9.5 g (0.01 mol) of Me$_2$SiHCl, and 9.1 g (0.1 mol) of methallyl chloride, followed by 0.015 ml Pt catalyst solution at 50° C. There was an exothermic reaction to 96° C. in 6 min. The complete reaction was vacuum distilled yielding 13.28 g (71.8%) of Me$_2$SiClCH$_2$CHMeCH$_2$Cl and 8.63 g (27.6%) of M$_2$D'CH$_2$CHMeCH$_2$Cl. This example indicates that neither MD'M nor Me$_2$SiHCl is an effective promoter for reaction of the other with methallyl chloride when used at the equimolar level. The yield based on methallyl chloride was 99.4%, indicating very efficient reaction of the olefinic reactant.

drosiloxane. The order of reactivity for greatest yield production is as follows: Cl$_3$SiH > MeSiHCl$_2$ > Et$_3$SiH. As observed in Comparative Example I, Me$_2$SiHCl actually interfered rather than promoted the reaction with MD'M since 71.8% of the yield was Me$_2$SiClCH$_2$CHMeCH$_2$Cl rather than the desired M$_2$D'CH$_2$CHMeCH$_2$Cl.

Comparative Example J

Reaction of Et$_3$SiH with methallyl chloride.

A mixture of Et$_3$SiH (10.5 g, 0.09 mol) and methallyl chloride (8.2 g, 0.09 mol) was combined in a 150 ml apparatus and 0.05 ml Pt catalyst solution added, followed by heating at reflux (115° C.) for 50 hr. Additional Pt catalyst solution (0.025 ml) was added at 40 hr. The incomplete reaction was distilled, yielding 4.98 g (36.8%) of Et$_3$SiCl and 3.48 g (18.7%) of Et$_3$SiCH$_2$CHMeCH$_2$Cl. This example shows that the unpromoted reaction of Et$_3$SiH with methallyl chloride is very slow and endothermic.

Example 8

Reaction of equimolar mixture of Et$_3$SiH/Cl$_3$SiH with methallyl chloride.

In a 100 ml apparatus, there were combined 11.6 g (0.1 mol) of Et$_3$SiH, 13.6 g (0.1 mol) of Cl$_3$SiH, and 9.1 g of methallyl chloride, followed by addition of 0.05 ml Pt catalyst solution at 21° C. There was a rapid and exothermic reaction to 61° C. in 2 min. Reaction appeared to have stopped and was heated to reflux over 4 hrs. when VPC showed complete reaction. Vacuum distillation yielded 17.03 g (82.5%) of Et$_3$SiCH$_2$CHMeCH$_2$Cl, indicating that Cl$_3$SiH is an effective promoter for the reaction of Et$_3$SiH with methallyl chloride.

Example 9

Reaction of Et$_3$SiH with methallyl chloride promoted by 10 mol-% Cl$_3$SiH.

The reaction of Example 14 was repeated except that only 1.3 g of Cl$_3$SiH was used. The reaction exothermed from 21° C. to 118.5° C. in 3 min, when reaction was complete. Vacuum distillation yielded 18.2 g (88.1%) of Et$_3$SiCH$_2$CHMeCH$_2$Cl. This example shows that the use of 10 mol-% Cl$_3$SiH as promoter for the reaction between Et$_3$SiH and methallyl chloride reduces reaction time by a factor of 1,000, increases the yield of the desired hydrosilation product by a factor of 5, and eliminates the need for external heating, relative to the unpromoted reaction of Comparative Example J. It also demonstrates that 10 mol-% Cl$_3$SiH is more effective than equimolar Cl$_3$SiH in promoting this reaction.

TABLE II

| PROMOTION OF MD'M AND METHALLYL CHLORIDE | | | | | |
|---|---|---|---|---|---|
| Example | REACTANT A | OLEFIN | PROMOTER | YIELD % | TIME |
| Comp. G | MD'M | CH$_2$=CMeCH$_2$Cl | — | 34.1* | 120 min |
| Comp. H | MD'M | CH$_2$=CMeCH$_2$Cl | — | 50.2 | 90 min |
| 5 | MD'M | CH$_2$=CMeCH$_2$Cl | EqM. Cl$_3$SiH | 81.8 | 1 min |
| 6 | MD'M | CH$_2$=CMeCH$_2$Cl | EqM. MeSiHCl$_2$ | 70.7 | 50 min |
| 7 | MD'M | CH$_2$=CMeCH$_2$Cl | EqM. Et$_3$SiH | 51.3 | 80 min |
| Comp. I | MD'M | CH$_2$=CMeCH$_2$Cl | EqM. Me$_2$SiHCl | 27.6+ | 6 min |

*When Olefin was later added to hydrosiloxane rather than at start, the yield was 50.2% (see Comparative Example H).
+Me$_2$SiHCl competed rather than promoted production with MD'M.

As can be seen from Table II, Cl$_3$SiH is again the best promoter (almost 300% relative increase) in the reaction of MD'M with methallyl chloride to produce M$_2$D'CH$_2$CHMeCH$_2$Cl. This increased yield is particularly significantly because it represents an accurate chemical model for a commercially used polyhy-

Comparative Example J'

Reaction of $Et_3SiH$ with methallyl chloride promoted by 13 mol-% $MeSiCl_3$.

The reaction of Example 9 was repeated except that 2.0 g $MeSiCl_3$ was used instead of $Cl_3SiH$. The reaction was heated up to 96° C. over 8 hr, and the complete reaction vacuum distilled, yielding 10.06 g (48.7%) of $Et_3SiCH_2CHMeCH_2Cl$. This example shows that $MeSiCl_3$ is a promoter but less effective than $Cl_3SiH$ for the reaction of $Et_3SiH$ with methallyl chloride.

Comparative Example L

Reaction of equimolar mixture of $Et_3SiH/MeSiHCl_2$ with methallyl chloride.

Comparative Example K

Reaction of $Et_3SiH$ with methallyl chloride promoted by 10 mol-% $Cl_3CH$.

In a 50 ml apparatus, there were combined 7.0 g (0.06 mol) of $Et_3SiH$, 5.4 g (0.06 mol) of methallyl chloride, and 0.7 g (0.006 mol) of trichloromethane, followed by addition of 0.02 ml of Pt catalyst solution at 37° C. Heat was applied up to 80° C. over 2 hr. Analysis by VPC showed no reaction, indicating that $Cl_3CH$ is ineffective as a promoter for the reaction of $Et_3SiH$ with methallyl chloride. Note that $Cl_3CH$ is the carbon analog of $Cl_3SiH$.

TABLE III

| | PROMOTION OF $Et_3SiH$ AND METHALLYL CHLORIDE | | | | |
|---|---|---|---|---|---|
| Example | REACTANT A | OLEFIN | PROMOTER | YIELD % | TIME |
| Comp. J | $Et_3SiH$ | $CH_2=CMeCH_2Cl$ | — | 18.7 | 3000 min |
| 8 | $Et_3SiH$ | $CH_2=CMeCH_2Cl$ | EqM. $Cl_3SiH$ | 82.5 | 242 min |
| 9 | $Et_3SiH$ | $CH_2=CMeCH_2Cl$ | 10 mol % $Cl_3SiH$ | 88.1 | 3 min |
| Comp J' | $Et_3SiH$ | $CH_2=CMeCH_2Cl$ | 13 mol % $MeSiCl_3$ | 48.7 | 480 min |
| Comp K | $Et_3SiH$ | $CH_2=CMeCH_2Cl$ | 10 mol % $Cl_3CH$ | — | 120 min |
| Comp L | $Et_3SiH$ | $CH_2=CMeCH_2Cl$ | $MeSiHCl_2$ | 20.9** | |
| Comp M | $Et_3SiH$ | $CH_2=CMeCH_2Cl$ | $Me_2SiHCl$ | 3.6** | |
| 11 | $Et_3SiH$ | $CH_2=CMeCH_2Cl$ | 10 mol % $Cl_3SiH$ | 49.7 | 98 min |

**In both cases, both $MeSiHCl_2$ and $Me_2SiHCl$ are in competition with the reactant rather than promoting it thus accounting for the low yields of $Et_3SiCH_2CHMeCH_2Cl$.

In a 100 ml apparatus, there were combined 11.6 g (0.1 mol) of $Et_3SiH$, 11.5 g (0.1 mol) of $MeSiHCl_2$, and 9.1 g (0.1 mol) of methallyl chloride. After heating to 50° C., the heat source was removed and 0.05 ml Pt catalyst solution added, causing an exothermic reaction to 83.5° C. in 4 min. The complete reaction was vacuum distilled, yielding 13.83 g (67.3%) of $MeSiCl_2CH_2CH-MeCH_2Cl$ and 4.31 g (20.9%) of $Et_3SiCH_2CH-MeCH_2Cl$. This example shows that while $MeSiHCl_2$ at the equimolar level promotes the reaction between $Et_3SiH$ and methallyl chloride, it also competes with $Et_3SiH$, reducing the yield of $Et_3SiCH_2CHMeCH_2Cl$.

Comparative Example M

Reaction of equimolar mixture of $Et_3SiH/Me_2SiHCl$ with methallyl chloride.

In a 100 ml apparatus, there were combined 7.1 g (0.075 mol) of $Me_2SiHCl$, 8.7 g (0.075 mol) of $Et_3SiH$, and 6.8 g (0.075 mol) of methallyl chloride. Pt catalyst solution (0.01 ml) was added at 32° C., causing an exothermic reaction to 94° C. in 4 min. Distillation of the complete reaction yielded 81.1% $Me_2SiClCH_2CH-MeCH_2Cl$ and 3.6% $Et_3SiCH_2CHMeCH_2Cl$. $Et_3SiH$ does promote slightly the reaction of $Me_2SiHCl$ with methallyl chloride.

Example 11

Reaction between $Et_3SiH$ and methallyl chloride promoted by $Cl_3SiH$ at sub-ambient temperature.

In a 50 ml apparatus, there was combined 11.6 g (0.1 mol) of $Et_3SiH$, 9.1 g (0.1 mol) of methallyl chloride, and 1.4 g (0.01 mol) of $Cl_3SiH$. The reaction mixture was cooled to 1° C. and was catalyzed with 0.05 ml of Pt catalyst solution. After 98 min at 1°–6° C., VPC analysis showed 47.9% conversion of reactants to $Et_3SiCH_2CHMeCH_2Cl$ with a $Et_3SiCH_2CHMeCH_2Cl/Et_3SiCl$ selectivity ratio of 24. This example shows that $Cl_3SiH$ is an effective promoter for the reaction between $Et_3SiH$ and methallyl chloride even at subambient temperatures.

From Table III, it can be seen that the most dramatic improvement in yield and in time are once more with $Cl_3SiH$ (almost 500% relative yield increase). Another important advantage of the invention is illustrated by Example 11. Example 11 is very significant because promotion is being done at subambient temperatures. The lowest temperature tested was 0° C. but this was by no means the lower limit. This is apparently the first example of a low temperature, platinum-catalyzed hydrosilation reaction involving a trialkylsilane.

The most effective promoter tested with these reactants was $Cl_3SiH$. Comparative Example K is to illustrate that the non-siloxane $Cl_3CH$ has no promotional effect.

Comparative Example N

Reaction of $Et_3SiH$ with methallyl chloride promoted by $SnCl_2$.

A solution of 0.43 g $SnCl_2.2H_2O$ in 5.0 g of Pt catalyst solution was prepared. A 50 ml apparatus was charged with 10.5 g (0.09 mol) of $Et_3SiH$ and 9.2 g (0.09 mol) of methallyl chloride, and the contents heated to 62° C. The Pt/Sn solution (0.05 ml) was added, and heat applied to reflux (83° C.) over 3 hr 40 min. VPC analysis showed no enhancement of $Et_3SiCH_2CHMeCH_2Cl$ yield, indicating that the $H_2PtCl_6/SnCl_2$ couple as disclosed in prior art (U.S. Pat. No. 4,089,882) is an ineffective hydrosilation catalyst for this reaction.

Example 12

Reaction of $Et_3SiH$ with methallyl chloride promoted by $F_3SiH$.

Gaseous $F_3SiH$ was generated by adding $Cl_3SiH$ to $\phi SiF_3$ containing $Bu_3N$ and the $F_3SiH$ so generated was bubbled through a reaction mixture of 11.6 g (0.1 mol) of $Et_3SiH$, 9.1 g (0.1 mol) of methallyl chloride, and 0.02 ml Pt catalyst solution for 20 min periods at 21°–48° C., with reaction being stirred at room temperature between periods. Analysis by VPC showed 34.6% conversion of reactants to $Et_3SiCH_2CHMeCH_2Cl$ with a $Et_3SiCH_2CHMeCH_2Cl/Et_3SiCl$ ratio of 24 on a weight basis. This example shows that $F_3SiH$ does promote the reaction of $Et_3SiH$ with methallyl chloride, but not as effectively as $Cl_3SiH$. $F_3SiH$ has the disadvantage of being a gas at room temperature, and is considered to be unstable.

Example 13

Reaction of $Et_3SiH$ with methallyl chloride promoted by $Br_3SiH$.

In a 50 ml apparatus, there were combined 11.6 g (0.1 mol) of $Et_3SiH$, 9.1 g (0.1 mol) of methallyl chloride, and 2.6 g (0.011 mol) of $Br_3SiH$. Pt catalyst solution was added (0.02 ml) at 60° C., followed by heating up to 70° C. over 100 min. Analysis by VPC showed 66.3% conversion of reactants to $Et_3SiCH_2CHMeCH_2Cl$, indicating that $Br_3SiH$ also promotes the reaction between $Et_3SiH$ and methallyl chloride, but not as effectively as $Cl_3SiH$. $Br_3SiH$ has the disadvantage of being pyrophoric.

Comparative Example O

Reaction of $Et_3SiH$ with methallyl chloride promoted by $Cl_3GeH$.

In a 50 ml apparatus, there were combined 11.6 g (0.1 mol) of $Et_3SiH$, 9.1 g (0.1 mol) of methallyl chloride, and 0.05 ml of Pt catalyst solution. $Cl_3GeH$ (0.18 g, 0.001 mol) was added at 23° C., with an additional 0.09 g being added 19 min later. Reaction was heated to 68° C. over 51 min and allowed to stand overnight at room temperature. Analysis by VPC showed no formation to $Et_3SiCH_2CHMeCH_2Cl$ indicating that $Cl_3GeH$ is not an effective promoter for the reaction of $Et_3SiH$ with methallyl chloride.

Comparative Example P

Reaction of $Et_3SiH$ with methallyl chloride promoted by $PCl_3$.

The reaction of Comparative Example O was repeated, except that in one case, 1.4 g of $PCl_3$ was used instead of $Cl_3GeH$, and in the other case, 0.05 ml $PCl_3$ was precombined with the 0.05 ml Pt catalyst solution. In neither case was there any formation of $Et_3SiCH_2CHMeCH_2Cl$ even after heating several hours, indicating $PCl_3$ is not an effective promoter for the reaction between $Et_3SiH$ and methallyl chloride.

In a 50 ml apparatus, there were combined 13.6 g (0.1 mol) of $Cl_3SiH$ and 9.1 g (0.1 mol) of methallyl chloride, followed by 0.05 ml Pt catalyst solution. Reaction was heated to reflux (44° C.) in 55 min, and was heated at reflux temp. which increased to 84° C. after 6 hr, followed by standing at room temp. overnight. VPC analysis indicated 67.3% conversion of reactants to a single product, $Cl_3SiCH_2CHMeCH_2Cl$. This example shows that the unpromoted reaction of $Cl_3SiH$ with methallyl chloride is relatively slow.

Example 14

Reaction of $Cl_3SiH$ with methallyl chloride promoted by $Et_3SiH$.

The reaction of Comparative Example Q was repeated except that 0.08 g (0.5 mol-%) of $Et_3SiH$ was added after the Pt catalyst. The reaction was heated intermittently up to 100° C. over 170 min, followed by vacuum distillation, which yielded 19.73 g (87.3%) of $Cl_3SiCH_2CHMeCH_2Cl$. This example shows that low levels of $Et_3SiH$ effectively promote the reaction between $Cl_3SiH$ and methallyl chloride.

Comparative Example R

Reaction of equimolar mixture of $Cl_3SiH/MeSiHCl_2$ with methallyl chloride.

In a 100 ml apparatus, there as combined 13.6 g (0.1 mol) of $Cl_3SiH$, 9.1 g (0.1 mol) of methallyl chloride, and 11.5 g (0.1 mol) of $MeSiHCl_2$, followed by 0.05 ml Pt catalyst solution at 21° C. Gentle heating caused an exothermic reaction to 52° C. in 22 min. The complete reaction was vacuum distilled, yielding 14.14 g (68.8%) of $MeSiCl_2CH_2CHMeCH_2Cl$ and 4.86 g (21.5%) of $Cl_3SiCH_2CHMeCH_2Cl$. This example indicates that at the equimolar level, neither $Cl_3SiH$ nor $MeSiHCl_2$ is an effective promoter for reactions of the other with methallyl chloride.

Comparative Example S

Reaction of equimolar mixture of $Cl_3SiH/Me_2SiHCl$ with methallyl chloride.

In a 50 ml apparatus, there was combined 7.1 g (0.075 mol) of $Me_2SiHCl$, 10.2 g (0.075 mol) of $Cl_3SiH$, and 6.8 g (0.075 mol) of methallyl chloride. Pt catalyst solution (0.02 ml) was added at 31° C. causing a violent exothermic reaction to more than 60° C. in 3 min. VPC analysis of the complete reaction showed 73.5% conversion to

TABLE IV

| | PROMOTIONAL EFFECTS OF OTHER PROMOTERS | | | | |
|---|---|---|---|---|---|
| Example | REACTANT A | OLEFIN | PROMOTER | YIELD % | TIME |
| Comp. J | $Et_3SiH$ | $CH_2=CMeCH_2Cl$ | — | 18.7 | 3000 min |
| Comp. N | $Et_3SiH$ | $CH_2=CMeCH_2Cl$ | $SnCl_2$* | =18.00 | 220 min |
| 12 | $Et_3SiH$ | $CH_2=CMeCH_2Cl$ | $F_3SiH$** | 34.6 | 60 min |
| 13 | $Et_3SiH$ | $CH_2=CMeCH_2Cl$ | $Br_3SiH$*** | 66.3 | 100 min |
| Comp. O | $Et_3SiH$ | $CH_2=CMeCH_2Cl$ | $Cl_3GeH$ | — | 51 min |
| Comp. P | $Et_3SiH$ | $CH_2=CMeCH_2Cl$ | $PCl_3$ | — | 7120 min |

*The Promoter was prepared as a 0.05 ml Pt/Sn solution when a solution of 0.43 g $SnCl_2$ and $2H_2O$ in 5.0 g of Pt catalyst solution were combined.
**Although some promotion is seen, $F_3SiH$ has the disadvantage of being a gas at room temperature and is considered to be unstable.
***$Br_3SiH$ has the disadvantage of being pyrophoric Table IV is to illustrate that the second silane really is the key to the invention since comparative experiments involving other promoters either do not function or have other serious problems associated with them.

Comparative Example Q

Reaction of $Cl_3SiH$ with methallyl chloride.

$Me_2SiClCH_2CHMeCH_2Cl$ and 2.9% conversion to $Cl_3SiCH_2CHMeCH_2Cl$. This example shows that $Cl_3SiH$ is an effective promoter for the reaction of $Me_2SiHCl$ with methallyl chloride, and suggests that lower levels of $Cl_3SiH$ would be just as effective.

TABLE V

PROMOTION OF Cl$_3$SiH AND METHALLYL CHLORIDE

| Example | REACTANT A | OLEFIN | PROMOTER | YIELD % | TIME |
|---------|------------|--------|----------|---------|------|
| Comp. Q | Cl$_3$SiH | CH$_2$=CMeCH$_2$Cl | — | 67.3 | 360 min |
| 14 | Cl$_3$SiH | CH$_2$=CMeCH$_2$CL | 0.5 mol % Et$_3$SiH | 87.3 | 170 min |
| Comp. R | Cl$_3$SiH | CH$_2$=CMeCH$_2$Cl | EqM. MeSiHCl$_2$ | 21.5** | 22 min |
| Comp. S | Cl$_3$SiH | CH$_2$=CMeCH$_2$Cl | EqM. Me$_2$SiHCl | 2.9** | |

**Here, 68.8% MeSiCl$_2$CH$_2$CHMeCH$_2$Cl are produced showing, if anything, Cl$_3$SiH slightly promotes MeSiHCl$_2$ rather than the other way around. With regard to Me$_2$SiHCl, 73.5% conversion to Me$_2$SiClCH$_2$CHMeCH$_2$Cl is effected showing Cl$_3$SiH is a good promoter for this reactant as well.

Table V shows that promotional effects depend on the nature of the reactant and promoter. If the promoter itself can compete with the reactant to react with the olefin, the reactant may in effect be acting as nothing more than a promoter itself as is seen in Comparative Examples R and S.

Comparative Example T

Reaction of MeSiHCl$_2$ with methallyl chloride.

In a 50 ml apparatus, there were combined 12.2 g (0.106 mol) of MeSiHCl$_2$ and 9.6 g (0.106 mol) of methallyl chloride, followed by 0.05 ml Pt catalyst solution at 21° C. Gentle heating caused a smooth exothermic reaction to 120° in 18 min. VPC analysis showed 97.7% conversion to MeSiCl$_2$CH$_2$CHMeCH$_2$Cl. This example shows that the unpromoted reaction of MeSiHCl$_2$ with methallyl chloride is relatively rapid, and the yield high.

Comparative Example U

Reaction of Me$_2$SiHCl with methallyl chloride.

In a 100 ml apparatus, there were combined 14.2 g (0.15 mol) of Me$_2$SiHCl and 13.6 g (0.15 mol) of methallyl chloride, followed by 0.05 ml Pt catalyst solution at 21° C. Gentle heating caused a smooth exothermic reaction to 90° C. in 16 in. Reaction was heated at 80° C. until completed (50 min). Vacuum distillation yielded 23.14 g (83.4%) of Me$_2$SiClCH$_2$CHMeCH$_2$Cl.

Comparative Example V

Reaction of equimolar mixture of equimolar mixture of MeSiHCl$_2$/Me$_2$SiHCl with methallyl chloride.

In a 100 ml apparatus, there were combined 8.6 g (0.75 mol) of MeSiHCl$_2$, 7.1 g (0.075 mol) of Me$_2$SiHCl, and 6.8 g (0.075 mol) of methallyl chloride. Pt catalyst solution (0.01 ml) was added at 32° causing an exothermic reaction to 57° C. and completion in 10 min. Distillation yielded 54.0% of Me$_2$SiClCH$_2$CHMeCH$_2$Cl and 19.6% of MeSiCl$_2$CH$_2$CHMeCH$_2$Cl, indicating that at the equimolar level, neither MeSiHCl$_2$ nor Me$_2$SiHCl is a very effective promoter for reactions of the other with methallyl chloride, in terms of yield, but that reaction rates are increased.

TABLE VI

PROMOTION OF MeSiHCl$_2$ AND Me$_2$SiHCl AND METHALLYL CHLORIDE

| Example | REACTANT A | OLEFIN | PROMOTER | YIELD % | TIME |
|---------|------------|--------|----------|---------|------|
| Comp. T | MeSiHCl$_2$ | CH$_2$=CMeCH$_2$Cl | — | 97.7* | 18 min |
| Comp. U | Me$_2$SiHCl | CH$_2$=CMeCH$_2$Cl | — | 83.4* | 50 min |

*As already suggested from some of the other examples (e.g., Comparative examples L, M, R and S), both these reactants react relatively well with methallyl chloride even without promotion. Neither, however, is a very effective promoter for the other (see Comparative Example V).

Comparative Example W

Reaction of Et$_3$SiH with methallyl chloride promoted by Cl$_3$SiH using other noble metal catalysts.

A standard solution of 69.8 g (0.6 mol) of Et$_3$SiH, 54.3 g (0.6 mol) of methallyl chloride, and 8.1 g (0.6 mol) of Cl$_3$SiH was made up to simulate the stoichiometry of Example 9. Other noble metal hydrosilation catalyst including platinum acetylacetonate, ethylene platinous chloride, platinum on carbon, bis(triphenylphosphine) platinum dichloride, ruthenium acetylacetonate, dichlorodicarbonyl-bis(triphenylphosphine) ruthenium, rhodium dicarbonyl dichloride dimer, and chloroiridic acid hexahydrate were tested at appropriate concentrations in aliquots of the standard solution. Only ethylene platinous chloride was as effective as the standard H$_2$PtCl$_6$ catalyst solution, with none being more effective. This example indicates that only soluble Pt compounds not containing strongly bound ligands such as acetylacetonate or phosphine groups are effective catalysts in the processes of the present invention. Note, in particular, that platinum on carbon (Pt/C) was ineffective at the lower temperatures (ambient or sub-ambient) where H$_2$PtCl$_6$ is effective, differentiating the instant invention from the prior art. The compounds (CH$_2$P$\phi_2$)$_2$PtClSiMe$_3$, (CH$_2$P$\phi_2$)$_2$Pt(SiMe$_3$)$_2$ and and [CH$_2$(P$\phi_2$)$_2$PtCl]$_2$ were also ineffective as catalysts in the above standard reaction.

Comparative Example X

Reaction of D$_3$D' with allyl chloride; reactants combined at start.

In a 100 ml flask there were combined 62.0 g of 90% D$_3$D' (containing 0.2 mol of D$_3$D'), 17.0 g (0.22 mol) of allyl chloride, and 0.2 ml of the catalyst used in Comparative Example A. Heat was applied to reflux temperature which increased gradually from 68° C. to 125° C. over 1.5 hrs. The reaction mixture was suction filtered into a 100 ml distillation flask and distilled, yielding the following products:

| Product | Boiling Point/ Pressure | g | Yield |
|---------|-------------------------|------|-------|
| D$_3$D'Cl | 33°/0.3 mm | 37.8 | 59.7% |
| D$_3$D'CH$_2$CH$_2$CH$_3$ | 44°/0.3 mm | 4.0 | 6.2% |
| D$_3$D'CH$_2$CH$_2$CH$_2$Cl* | 63°/0.2 mm | 8.0 | 11.2% |
| D$_3$D'CH$_2$CH$_2$CH$_2$D'D$_3$ | 117°/0.25 mm | 2.4 | — |

*The yield of the desired hydrosilation product was only 11.2%

Comparative Example Y

Reaction of D$_3$D' with allyl chloride; olefin added to hydrosiloxane.

In the apparatus of Comparative Example X, there were placed 56.4 g (0.2 mol) of $D_3D'$ which was heated to 78° C., when 0.2 ml of the catalyst used in Example 2 was added. Dropwise addition of 15.3 g (0.2 mol) of allyl chloride was begun and the reaction temperature was maintained at 95°–124° C. until completion (37 mins). The reaction mixture was distilled yielding the following products:

| Product | Boiling Point/ Pressure | g | Yield |
|---|---|---|---|
| $D_3D'Cl$ | 27°/0.7 mm | 22.0 | 34.8% |
| $D_3D'CH_2CH_2CH_3$ | 29°/0.7 mm | 16.6 | 33.0% |
| $D_3D'CH_2CH_2Cl$* | 53°/0.2 mm | 13.9 | 19.4% |
| $D_3D'CH_2CH_2D'D_3$ | — | trace | — |
| Heavies | — | 1.6 | — |

*The yield of the desired hydrosilation product was 19.4%, a 73.2% relative improvement over the 11.2% obtained in Comparative Example G.

Example 15

Reaction of equimolar mixture of $D_3D'/Cl_3SiH$ with allyl chloride.

In a 100 ml apparatus, there were combined 15.5 g (0.114 mol) of $Cl_3SiH$, 32.3 g (0.114 mol) of $D_3D'$ and 8.8 g (0.114 mol) of allyl chloride. Pt catalyst solution (0.05 ml) was added at 21° C., causing a gentle exothermic reaction to 83° C. in 52 min. Vacuum distillation yielded 7.02 g (29.0%) of $Cl_3SiCH_2CH_2CH_2Cl$ and 10.2 g (24.9%) of $D_3CH_2CH_2CH_2Cl$. This example shows that $Cl_3SiH$ at the equimolar level increases both rate and yield of the reaction between $D_3D'$ and allyl chloride.

Example 16

Reaction of equimolar mixture of $D_3D'/MeSiHCl_2$ with allyl chloride.

In a 100 ml apparatus, there were combined 15.8 g (0.14 mol) of $MeSiHCl_2$, 38.6 g (0.14 mol) of $D_3D'$, and 10.5 g (0.1 mol) of allyl chloride. Pt catalyst solution (0.05 ml) was added at 19° C. and the reaction mixture allowed to stir overnight at 28° C. (heat generated by magnetic stirrer). Gentle heat was applied to the unreacted mixture, causing an exothermic reaction to 95° C. in 45 min. Vacuum distillation yielded 5.82 g (22.2%) of $MeSiCl_2CH_2CH_2CH_2Cl$ and 15.65 g (31.8%) of $D_3D'CH_2CH_2CH_2Cl$, indicating that at the equimolar level, $MeSiHCl_2$ is more effective than $Cl_3SiH$ at increasing the yield of the reaction between $D_3D'$ and allyl chloride.

Comparative Example Z

Reaction of equimolar mixture of $D_3D'/MeSiHCl_2$ with allyl chloride in the presence of tributylamine.

The reaction of Example 16 was repeated except at 0.1 mol of each reactant was used and 0.05 ml of $Bu_3N$ was added after the Pt catalyst. The reaction exothermed from 22° C. to 48° C. in 108 min, and was vacuum distilled, yielding 10.09 g (52.7%) of $MeSiCl_2CH_2CH_2CH_2Cl$ and 0.8 g (2.2%) of $D_3D'CH_2CH_2CH_2Cl$. The tertiary amine promoter ($Bu_3N$ is claimed as a promoter for $MeSiHCl_2$ in its reaction with allyl chloride) enhances the hydrochlorosilane reactivity, and interferes with the hydrochlorosilane promotion of the hydrosiloxane reactivity. Note that the relative reactivities of $D_3D'$ and $MeSiHCl_2$ are reversed in Examples 16 and Comparative Example Z.

Example 17

Reaction of equimolar mixture of $D_3D'/Et_3SiH$ with allyl chloride.

In a 100 ml apparatus, there were combined 28.3 g (0.1 mol) of 98% $D_3D'$, 11.6 g (0.1 mol) of $Et_3SiH$, and 7.7 g (0.1 mol of allyl chloride. Pt catalyst solution (0.05 ml) was added at 22° C., followed by heating up to 66° C. over 145 min. Vacuum distillation yielded 7.15 g (19.9%) of $D_3D'CH_2CH_2CH_2Cl$, and a trace of $Et_3SiCH_2CH_2CH_2Cl$. This example shows that neither $D_3D'$ nor $Et_3SiH$ are very effective promoters at the equimolar level for reactions of the other with allyl chloride.

Example 18

Reaction of equimolar mixture of $D_3D'/MD'M$ with allyl chloride.

In a 100 ml apparatus, there were combined 22.2 g (0.1 mol of $MD'M$, 30.5 g (0.1 mol) of 92% $D_3D'$, and 7.7 g (0.1 mol) of allyl chloride. Pt catalyst solution (0.05 ml) was added at 25° C., and heat applied to 80° C. over 40 min, followed by an exothermic reaction to 140° C. over 15 min. Vacuum distillation yielded 1.15 g (3.9%) of $M_2D'CH_2CH_2CH_2Cl$ and 6.91 g (19.3%) of $D_3D'CH_2CH_2CH_2Cl$, indicating that neither $D_3D'$ nor $MD'M$ are very effective promoters for reaction of the other with allyl chloride when used at the equimolar level.

Example 19

Reaction of equimolar mixture of $D_3D'/Me_2SiHCl$ with allyl chloride.

In a 100 ml apparatus, there were combined 30.5 g (0.1 mol) of 92% $D_3'$, 9.5 g (0.1 mol) of $Me_2SiHCl$, and 7.7 g (0.1 mol) of allyl chloride. Pt catalysts solution (0.05 ml was added at 42° C. and heat applied to 97.5° C. over 144 min. Vacuum distillation yielded 3.99 g (23.3%) of $Me_2SiClCH_2CH_2CH_2Cl$ and 11.15 g (31.1%) of $D_3D'CH_2CH_2CH_2Cl$. This example shows that $Me_2SiHCl$ is slightly less effective than $MeSiHCl_2$ in promoting the reaction between $D_3D'$ and allyl chloride when used at the equimolar level.

TABLE VII

| PROMOTION OF $D_3D'$ AND ALLYL CHLORIDE | | | | | |
|---|---|---|---|---|---|
| Example | REACTANT A | OLEFIN | PROMOTER | YIELD % | TIME |
| Comp. X | $D_3D'$ | $CH_2=CHCH_2Cl$ | — | 11* | 90 min |
| Comp. Y | $D_3D'$ | $CH_2=CHCH_2Cl$ | — | 19.4 | 37 min |
| 15 | $D_3D'$ | $CH_2=CHCH_2Cl$ | EqM. $Cl_3SiH$ | 24.9 | 52 min |
| 16 | $D_3D'$ | $CH_2=CHCH_2Cl$ | EqM. $MeSiHCl_2$ | 31.8 | 45 min |
| Comp. Z | $D_3D'$ | $CH_2=CHCH_2Cl$ | EqM. $MeSiHCl_2$ and tributylamine | 2.2 | 108 min |
| 17 | $D_3D'$ | $CH_2=CHCH_2Cl$ | EqM. $Et_3SiH$ | 19.9 | 145 min |
| 18 | $D_3D'$ | $CH_2=CHCH_2Cl$ | EqM. $MD'M$ | 19.3 | 55 min |

TABLE VII-continued

PROMOTION OF $D_3D'$ AND ALLYL CHLORIDE

| Example | REACTANT A | OLEFIN | PROMOTER | YIELD % | TIME |
|---------|------------|--------|----------|---------|------|
| 19 | $D_3D'$ | $CH_2=CHCH_2Cl$ | EqM. $Me_2SiHCl$ | 31.1 | 144 min |

*When the olefin was later added to the hydrosiloxane rather than at the start, the yield was improved to 19.4% (see Comparative Example Y).

Several observations may be made from Table VII. First, Comparative Example Z shows how tributylamine interferes with promotion relative to Example 16.

Second, comparing Table VII to Table I, it can be seen that the yields of the reaction may vary merely by changing the olefin reactant. For example, both $MeSiHCl_2$ and $MeSiHCl$ are stronger promoters than $Cl_3SiH$ when using allyl chloride while, when methallyl chloride is used as the reactant olefin (Table I), the opposite is true.

Comparative Example AA

Reactant of MD'M with allyl chloride.

In a 100 ml apparatus, there were combined 22.3 g (0.1 mol) of MD'M and 7.7 g (0.1 mol) of allyl chloride. Pt catalyst solution (0.05 ml) was added at 48° C., causing a gradual exothermic reaction to 120° C. in 41 min. Vacuum distillation yielded 4.50 g (15.1%) of $M_2D'CH_2CH_2CH_2Cl$ as one of the several products.

Comparative Example BB

Reaction of MD'M with allyl chloride promoted by $SnCl_2$.

The reaction of Comparative Example AA was repeated except that the Pt/Sn catalyst solution of Comparative Example K was used instead of the standard $H_2PtCl_6$ solution. There was an exothermic reaction from 45° C. to 73° C. over 53 min. VPC analysis showed $M_2D'Cl$ was the major product with only a trace of $M_2D'CH_2CH_2CH_2Cl$, such that $SnCl_2$ does not promote the hydrosilation reaction between MD'M and allyl chloride.

Example 20

Reaction of equimolar mixture of MD'M/$Cl_3SiH$ with allyl chloride.

In a 100 ml apparatus, there were combined 11.1 g (0.05 mol) of MD'M, 6.8 g (0.05 mol) of $Cl_3SiH$, and 3.9 g (0.05 mol) of allyl chloride. Pt catalyst solution (0.025 ml) was added at 23° C., causing a violent exothermic reaction to 96° C. in 3 min. Vacuum distillation yielded 0.13 g of $Cl_3SiCH_2CH_2CH_2Cl$ and 5.99 g (40.1%) of $M_2D'CH_2CH_2CH_2Cl$. This example shows that $Cl_3SiH$ at the equimolar level is an effective promoter for the reaction of MD'M with allyl chloride, enhancing both rate and yield relative to the unpromoted reaction of Comparative Example AA.

Example 21

Reaction of equimolar mixture of MD'M/$MeSiHCl_2$ with allyl chloride.

In a 100 ml apparatus, there were combined 16.7 g (0.075 mol) of MD'M, 8.6 g (0.075 mol) of $MeSiHCl_2$, and 5.7 g (0.075 mol) of allyl chloride. Pt catalyst solution (0.01 ml) was added at 54° C. and the reaction heated up to 84° C. over 2 hr. Vacuum distillation yielded 44.4% of $M_2D'CH_2CH_2CH_2Cl$ and 7.6% of $MeSiCl_2CH_2CH_2CH_2Cl$. This example shows that $MeSiCl_2H$ at the equimolar level effectively enhances yield, but not rate, of the reaction between MD'M and allyl chloride.

Comparative Example CC

Reaction of equimolar mixture of MD'M/$Me_2SiHCl$ with allyl chloride.

In a 100 ml apparatus, there were combined 22.3 g (0.1 mol) of MD'M, 9.5 g (0.1 mol) of $Me_2SiHCl$, and 7.7 g (0.1 mol) of allyl chloride. Pt catalyst solution was added at 74° C. (0.05 ml), followed by heating up to 92° C. over 162 min. Vacuum distillation of the reaction yielded 18.1% of $M_2D'CH_2CH_2CH_2Cl$ and 10.3% of $Me_2SiClCH_2CH_2CH_2Cl$. This example shows that neither MD'M nor $Me_2SiHCl$ is an effective promoter at the equimolar level for reactions of the other with allyl chloride.

Example 22

Reaction of equimolar mixture of MD'M/$Et_3SiH$ with allyl chloride.

In a 100 ml apparatus, there were combined 11.1 g (0.05 mol) of MD'M, 5.8 g (0.05 mol) of $Et_3SiH$, and 3.8 g (0.05 mol) of allyl chloride. Pt catalyst solution (0.01 ml) was added at 54° C. and the reaction heated to 90° C. over 28 min. VPC analysis of the reaction mixture showed 23.9% of $M_2D'CH_2CH_2CH_2Cl$ and 7.2% $Et_3SiCH_2CH_2CH_2Cl$, indicating that both MD'M and $Et_3SiH$ are slightly effective promoters at the equimolar level for reactions of the other with allyl chloride.

TABLE VIII

PROMOTION OF MD'M AND ALLYL CHLORIDE

| Example | REACTANT A | OLEFIN | PROMOTER | YIELD % | TIME |
|---------|------------|--------|----------|---------|------|
| Comp. AA | MD'M | $CH_2=CHCH_2Cl$ | — | 15.1 | 41 min |
| Comp. BB | MD'M | $CH_2=CHCH_2Cl$ | $Sn_2Cl_2$* | — | 53 min |
| 20 | MD'M | $CH_2=CHCH_2Cl$ | EqM. $Cl_3SiH$ | 40.1 | 3 min |
| 21 | MD'M | $CH_2=CHCH_2Cl$ | EqM. $MeSiHCl_2$ | 44.4 | 120 min |
| Comp. CC | MD'M | $CH_2=CHCH_2Cl$ | EqM. $Me_2SiHCl$ | 18.1 | 162 min |
| 22 | MD'M | $CH_2=CHCH_2Cl$ | EqM. $Et_3SiH$ | 23.9 | 28 min |

*This was the same Pt/Sn catalyst solution of Comparative Example K.
**Because promotion was just under 20%, this was not included as an example of the invention.

Again, although Table II varies from Table VIII only by the olefin employed, differences are observed. For example, $MeSiHCl_2$ promotes greater yield than $Cl_3SiH$ (although rate is much slower). Both, however, are still greater than $Et_3SiH$ which in turn is greater than $Me_2SiHCl$.

Comparative Example DD

Reaction of Et$_3$SiH with allyl chloride.

In a 100 ml apparatus, there were combined 11.6 g (0.1 mol) of Et$_3$SiH, 7.7 g (0.1 mol of allyl chloride, and 0.05 ml Pt catalyst solution at 19° C. After stirring 1 hr, temperature had increased to 27° C., followed by heating at 70° C. for 17 hr. The incomplete reaction was vacuum distilled, yielding 8.9 g (42%) of Et$_3$SiCl, and 3.0 g (15.5%) of Et$_3$SiCH$_2$CH$_2$CH$_2$Cl. The Et$_3$SiCH$_2$CH$_2$C$_2$Cl/Et$_3$SiCl molar selectivity ratio was 0.37. This example shows that the unpromoted reaction between Et$_3$SiH and CH$_2$=CHCH$_2$Cl is very slow.

Comparative Example EE

Reaction of equimolar mixture of Et$_3$SiH/Cl$_3$SiH with allyl chloride.

In a 50 ml apparatus, there were combined 11.6 g (0.01 mol) of Et$_3$SiH, 13.6 g (0.1 mol) of Cl$_3$SiH, and 7.7 g (0.01 mol) of allyl chloride. Pt catalyst solution (0.05 ml) was added, causing a gentle exothermic reaction from 19° C. to 36° C. in 35 min. Heat was applied up to 66° C. over the next 75 min. Vacuum distillation yielded 0.80 g (4.2%) of Et$_3$SiCH$_2$CH$_2$CH$_2$Cl and 11.48 g (54.2%) of Cl$_3$SiCH$_2$CH$_2$CH$_2$Cl. This example shows that Et$_3$SiH at the equimolar level is an effective promoter for the reaction between Cl$_3$SiH and allyl chloride, since that reaction is very slow at reflux temperature in the absence of a promoter.

Comparative Example FF

Reaction of equimolar mixture of Et$_3$SiH/Cl$_3$SiH with allyl chloride, latter added to former.

The reaction of Comparative Example EE was repeated except that the allyl chloride was added dropwise to a mixture of the two silanes and the Pt catalyst beginning at 39° C. There was a smooth exothermic reaction up to 80° over the addition (30 min) followed by 15 min at 80° C. Vacuum distillation yielded 3.17 g (16.5%) of Et$_3$SiCH$_2$CH$_2$CH$_2$Cl, and 10.67 g (50.3%) of Cl$_3$SiCH$_2$CH$_2$CH$_2$Cl. This example shows that adding the olefin as above allows both Cl$_3$SiH and Et$_3$SiH to promote the hydrosilation reaction rate of the other toward allyl chloride. Selectivity and yield were also improved for Et$_3$SiH, with a Et$_3$SiCH$_2$CH$_2$Cl/Et$_3$SiCl molar selectivity ratio of 2.5.

Example 23

Reaction of equimolar mixture of Et$_3$SiH/Cl$_3$SiH with allyl chloride, former added to latter.

The reaction of Comparative Example FF was repeated except that the silane mixture was added dropwise to the allyl chloride containing the Pt catalyst, beginning at 40.5° C. Heat was applied up to 50° C. over 132 min (time of addition). Vacuum distillation yielded 6.30 g (32.7%) of Et$_3$SiCH$_2$CH$_2$CH$_2$Cl and 7.71 g (36.4%) of Cl$_3$SiCH$_2$CH$_2$CH$_2$Cl. This example shows that while this sequence of combination of reactants causes a lower reaction rate, yield and selectivity of the Et$_3$SiH reaction with allyl chloride are improved further. The Et$_3$SiCH$_2$CH$_2$CH$_2$Cl/Et$_3$SiCl molar ratio was 2.82.

Example 24

Reaction of Et$_3$SiH with 10/1 molar mixture of allyl chloride/Cl$_3$SiH, latter added to former.

In a 25 ml apparatus, there were combined 11.6 g (0.1 mol) of Et$_3$SiH and 0.05 ml of Pt catalyst solution. Heat was applied to 60° C. and addition of a mixture of 7.7 g (0.1 mol) of allyl chloride and 1.4 g (0.01 mol) of Cl$_3$SiH begun. There was a smooth exothermic reaction up to 80° C. by the end of the addition (15 min) with temperature continuing to rise to 129° C. 5 min later. Vacuum distillation yielded 12.12 g (63.0%) of Et$_3$SiCH$_2$CH$_2$CH$_2$Cl, with a Et$_3$SiCH$_2$CH$_2$CH$_2$Cl/Et$_3$SiCl molar ratio of 2.73. This example shows that low levels of Cl$_3$SiH effectively promote both rate and yield of the reaction between Et$_3$SiH and allyl chloride, particularly when the low levels are maintained throughout the reaction by replenishment.

Example 25

Reaction of 8/1 molar mixture of Et$_3$SiH/Cl$_3$SiH with allyl chloride, latter added to former.

In a 100 ml apparatus, there were combined 11.6 g (0.1 mol) of Et$_3$SiH, 1.7 g (0.0125 mol) of Cl$_3$SiH and 0.05 ml of Pt catalyst solution. The mixture was heated to 65° C. and addition of 7.7 g (0.1 mol) of allyl chloride begun. There was an exothermic reaction to 108.5° C. over 16 min, followed by a temperature drop. Addition of allyl chloride was complete in 31 min, with heat then applied at reflux (up to 114° C.) over 170 min. Vacuum distillation yielded 7.88 g (40.9%) of Et$_3$SiCH$_2$CH$_2$CH$_2$Cl with a Et$_3$SiCH$_2$CH$_2$CH$_2$Cl/Et$_3$SiCl selectivity ratio of 1.13. This example shows that this sequence of combination of reactants allows the Cl$_3$SiH promoter to be consumed, at which point the reaction of Et$_3$SiH with allyl chloride proceeds at the low rate and selectivity exhibited in Comparative Example DD.

Example 26

Reaction of 10/1 molar mixture of Et$_3$SiH/Cl$_3$SiH with allyl chloride, former added to latter.

In a 50 ml apparatus, there were combined 7.7 g (0.1 mol) of allyl chloride and 0.05 ml of Pt catalyst solution. the mixture was heated to 44° C. and addition of a mixture of 11.6 g (0.1 mol) of Et$_3$SiH and 1.4 g (0.01 mol) of Cl$_3$SiH begun. Reaction was heated up to 54.5° C. during addition (30 min). There was a violent exothermic reaction from 62° C. to 110° C. 16 min later. Vacuum distillation yielded 7.79 g (40.5%) of Et$_3$SiCH$_2$CH$_2$CH$_2$Cl, with a Et$_3$SiCH$_2$CH$_2$CH$_2$Cl/Et$_3$SiCl selectivity ratio of 1.23. This example and the previous one show that the preferred sequence of combination of reactants for most effective Cl$_3$SiH promotion of the reaction of Et$_3$SiH with allyl chloride is that of Example 24.

Example 27

Reaction of Et$_3$SiH with allyl chloride using Cl$_3$SiH/H$_2$PtCl$_6$ solution as catalyst.

The reaction of Comparative Example DD was repeated except that 0.1 ml of the Cl$_3$SiH/H$_2$PtCl$_6$ catalyst solution of Example 16 was used instead of the standard H$_2$PtCl$_6$ solution. Heat was applied over 205 min up to 90° C., followed by vacuum distillation which yielded 4.36 g (22.6%) Et$_3$SiCH$_2$CH$_2$CH$_2$Cl, with a Et$_3$SiCH$_2$CH$_2$CH$_2$Cl/Et$_3$SiCl ratio of 0.35. This example shows that very low levels of Cl$_3$SiH cause modest rate increases in the reaction between Et$_3$SiH and allyl chloride, but do not affect selectivity.

TABLE IX
PROMOTION OF Et₃SiH AND ALLYL CHLORIDE

| Example | REACTANT A | OLEFIN | PROMOTER | YIELD % | TIME |
|---|---|---|---|---|---|
| Comp. DD | $Et_3SiH$ | $CH_2=CHCH_2Cl$ | — | 15.5 | 1000 min |
| Comp. EE | $Et_3SiH$ | $CH_2=CHCH_2Cl$ | EqM. $Cl_3SiH$* | 4.2 | 110 min |
| Comp. FF | $Et_3SiH$ | $CH_2=CHCH_2Cl$ | EqM. $Cl_3SiH$ | 16.5 | 45 min |
| 23 | $Et_3SiH$ | $CH_2=CHCH_2Cl$ | EqM. $Cl_3SiH$ | 32.7 | 132 min |
| 24 | $Et_3SiH$ | $CH_2=CHCH_2Cl$ | 10/1 Olefin/$Cl_3SiH$ | 63.0 | 20 min |
| 25 | $Et_3SiH$ | $CH_2=CHCH_2Cl$ | 13 mol. % $Cl_3SiH$ | 40.9 | 170 min |
| 26 | $Et_3SiH$ | $CH_2=CHCH_2Cl$ | 10 mol. % $Cl_3SiH$ | 40.5 | 46 min |
| 27 | $Et_3SiH$ | $CH_2=CHCH_2Cl$ | 0.1 ml $Cl_3Si/H_2PtCl_6$** | 22.6 | 205 min |

*Compare to Example 8 where, though only difference is in the olefin, the yield was 82.5%.
**When 0.1 ml (i.e. very small quantity of $Cl_3SiH$) of catalyst solution of Example 16 is used, modest increases are found again indicating the difference when only the olefin is charged.

Table IX again illustrates a number of interesting observations. First, in comparing Examples FF and 23 to Example EE, the only difference is in the order the reactants are combined. After the olefin to a mixture of $Et_3SiH$ and $Cl_3SiH$ promoter later rather than at the start increased the yield to 16.5% while, when $Et_3SiH$ and $Cl_3SiH$ were precombined and added to the olefin later, the yield rose to 32.7%.

Similarly, the order of combination effects lower yields in Examples 25 and 26 compared to Example 24. In Example 24, the olefin and $Cl_3SiH$ are given a chance to precombine before being added to $Et_3SiH$. By contrast, both the $Cl_3SiH$ and $Et_3SiH$ are precombined in Examples 25 and 26 whether they are added to the olefin (Example 26) or the olefin is later added to them (Example 25).

Finally, comparing Examples EE and 27 to Example 8 in Table III, it can be observed once more that yields may be greatly affected merely by changing the olefin of the reaction.

Comparative Example GG

Reaction of $Me_2SiHCl$ with allyl chloride.

In a 100 ml apparatus, there were combined 18.9 g (0.2 mol) of $Me_2SiHCl$, 15.3 g (0.2 mol) of allyl chloride, and 0.05 ml Pt catalyst solution at 18.5° C., followed by heating at reflux for 50 hr. An equivalent quantity of Pt catalyst solution was added during the reflux period. Vacuum distillation of the incomplete reaction yielded 12.6% of $Me_2SiClCH_2CH_2CH_2Cl$. This example shows that the unpromoted reaction of $Me_2SiHCl$ with allyl chloride proceeds very slowly at reflux temperature.

Example 28

Reaction of equimolar mixture of $Et_3SiH/Me_2SiHCl$ with allyl chloride.

In a 100 ml apparatus, there were combined 7.1 g (0.075 mol) of $Me_2SiHCl$, 8.7 g (0.075 mol) of $Et_3SiH$ and 5.7 g (0.075 mol) of allyl chloride. Pt catalyst solution was added (0.05 ml) at 34° C. Gentle heating caused a smooth exothermic reaction to 92° over 36 min. Vacuum distillation yielded 42.5% of $Me_2SiClCH_2CH_2CH_2Cl$ and 4.8% of $Et_3SiCH_2CH_2CH_2Cl$. This example shows that $Et_3SiH$ at the equimolar level is an effective promoter for the reaction between $Me_2SiHCl$ and allyl chloride.

Example 29

Reaction of equimolar mixture of $Et_3SiH/MeSiHCl_2$ with allyl chloride.

In a 100 ml apparatus, there were combined 11.6 g (0.1 mol) of $Et_3SiH$, 11.5 g (0.1 mol) of $MeSiHCl_2$, and 7.7 g (0.1 mol) of allyl chloride. Pt catalyst solution (0.05 ml) was added at 21° C., gentle heating caused an exothermic reaction to 88° C. over 150 min. Vacuum distillation yielded 40.4% of $MeSiCl_2CH_2CH_2CH_2Cl$ and 13.0% of $Et_3SiCH_2CH_2CH_2Cl$. This example shows that both $MeSiHCl_2$ and $Et_3SiH$ are promoters at the equimolar level for reactions of the other with allyl chloride. The promotion effects are milder than those between $Et_3SiH$ and $Cl_3SiH$ as shown in Comparative Example FF. The unpromoted reaction between $MeSiHCl_2$ and allyl chloride is known to be slow at reflux.

Comparative Example HH

Reaction of equimolar mixture of $Cl_3SiH/MeSiHCl_2$ with allyl chloride.

In a 50 ml apparatus, there were combined 13.1 g (0.097 mol) of $Cl_3SiH$, 11.1 g (0.097 mol) of $MeSiHCl_2$, and 7.4 g (0.097 mol) of allyl chloride. Pt catalyst solution (0.05 ml) was added at 21.5° C., causing a smooth exothermic reaction to 55° C. over 42 min, followed by heating at reflux (up to 67° C.) over 330 min. Vacuum distillation yielded 12.14 g of a mixture of $Cl_3SiCH_2CH_2CH_2Cl/MeSiCl_2CH_2CH_2CH_2Cl$ in a 2.04/1 ratio. This example shows that neither $Cl_3SiH$ nor $MeSiHCl_2$ is a very effective promoter at the equimolar level for reactions of the other with allyl chloride.

Comparative Example II

Reaction of equimolar mixture of $Cl_3SiH/Me_2SiHCl$ with allyl chloride.

In a 100 ml apparatus, there were combined 7.1 g (0.075 mol) of $Me_2SiHCl$, 10.2 g (0.075 mol) of $Cl_3SiH$, and 5.7 g (0.075 mol) of allyl chloride. Pt catalyst solution (0.01 ml) was added at 33° C., causing an exothermic reaction to 47° C. in 7 min. VPC analysis 14 min. later showed a complete reaction. Vacuum distillation yielded 60.4% $Cl_3SiCH_2CH_2CH_2Cl$ and 8.6% $Me_2SiClCH_2CH_2CH_2Cl$. This example shows that $Me_2SiHCl$ is an effective promoter for the reaction of $Cl_3SiH$ with allyl chloride at the equimolar level.

Example 30

Reaction of equimolar mixture of $MeSiHCl_2/Me_2SiHCl$ with allyl chloride.

In a 100 ml apparatus, there were combined 8.6 g (0.075 mol) of $MeSiHCl_2$, 7.1 g (0.075 mol) of $Me_2SiHCl$, and 5.7 g (0.075 mol) of allyl chloride. Pt catalyst solution (0.01 ml) was added at 37° C., followed by heating up to 45° C. over 1 hr. Vacuum distillation yielded 31.3% of $MeSiCl_2CH_2CH_2CH_2Cl$ and 22.6% of $Me_2SiClCH_2CH_2CH_2Cl$. This example shows that neither $Me_2SiHCl$ nor $MeSiHCl_2$ is a very effective promoter at the equimolar level for reactions of the other with allyl chloride.

TABLE X
PROMOTION OF Me$_2$SiHCl AND ALLYL CHLORIDE

| Example | REACTANT A | OLEFIN | PROMOTER | YIELD % | TIME |
|---|---|---|---|---|---|
| Comp. GG | Me$_2$SiHCl | CH$_2$=CHCH$_2$Cl | — | 12.6 | 3000 min |
| 28 | Me$_2$SiHCl | CH$_2$=CHCH$_2$Cl | EqM. Et$_3$SiH* | 42.5* | 36 min |
| Comp. II | Me$_2$SiHCl | CH$_2$=CHCH$_2$Cl | EqM. Cl$_3$SiH | 8.6 | 7 min |
| 30 | Me$_2$SiHCl | CH$_2$=CHCH$_2$Cl | EqM. MeSiHCl$_2$ | 22.6 | >60 min |

*Compare to Comparative Example M. Here the production from the corresponding olefin was 81.1%.

This Table shows again how varying the olefin and reactant also changes the yields. For example, the same quantity of Et$_3$SiH and Me$_2$SiHCl(Comparative Example M versus Example 28) promotes 81.1% yield with methallyl chloride and only 42.5% yield with allyl chloride.

Comparative Example JJ

Reaction of Cl$_3$SiH with allyl chloride, former added to latter.

In a 50 ml apparatus, there were combined 7.7 g (0.1 mol) of allyl chloride and 0.05 ml Pt catalyst solution. The mixture was heated to reflux (43° C.) and the addition of 13.6 g (0.1 mol) of Cl$_3$SiH begun. Addition was complete in 33 min, during which the reflux temp. had increased to 47° C. After another 16 min, reflux temp. was 70° C. and reaction was complete. Vacuum distillation yielded 14.01 g (66.1%) of Cl$_3$SiCH$_2$CH$_2$CH$_2$Cl. This example shows that the reaction between Cl$_3$SiH and allyl chloride, which is slow at the reflux temperature of the combined reactants, can be accelerated by beginning at the higher reflux temperature of the allyl chloride.

Comparative Example KK

Reaction of Cl$_3$SiH with allyl chloride promoted by Cl$_3$GeH.

The reaction of Comparative Example JJ was repeated except that all reactants and catalyst were combined at the start and 0.18 g of Cl$_3$GeH added at once (instead of Et$_3$SiH). VPC analysis showed no promotion of the reaction between Cl$_3$SiH and allyl chloride even after heating at reflux for 3 hr. Cl$_3$GeH is not an effective promoter for the reaction between Cl$_3$SiH and allyl chloride under these conditions.

Cl$_3$SiH and allyl chloride, increasing the reaction rate, but not the yield or selectivity.

Example 32

Reaction of 15/1 molar mixture of Cl$_3$SiH/Et$_3$SiH with allyl chloride, latter added to former.

In a 50 ml apparatus, there were combined 12.0 g (0.09 mol) of Cl$_3$SiH, 0.7 g (0.006 mol) of Et$_3$SiH, and 0.04 ml of Pt catalyst solution. The addition of 6.8 g (0.09 mol) of allyl chloride was begun at 24° C. causing an exothermic reaction to 63° C. during addition (18 min). Vacuum distillation yielded 11.92 g (63.2%) of Cl$_3$SiCH$_2$CH$_2$CH$_2$Cl, showing that Et$_3$SiH promotes the reaction between Cl$_3$SiH and allyl chloride at lower temperatures than phenothiazine, such that no external heating is required. This example also shows that the reactant combination sequence has little effect effect on yield or selectivity of the reaction between Cl$_3$SiH and allyl chloride.

Example 33

Reaction between Cl$_3$SiH and allyl chloride promoted by Et$_3$SiH.

To a mixture of 13.6 g (0.1 mol) of Cl$_3$SiH and 0.05 ml Pt catalyst solution in a 50 ml apparatus, there was added dropwise 7.7 g (0.1 mol) of allyl chloride at 24° C. VPC analysis 1 hr. after start of addition (30 min. after completion of addition) showed less than 1% conversion of reactants to products. Et$_3$SiH (0.04 ml) was added, causing a smooth exothermic reaction to 67° C. in 24 min. Vacuum distillation yielded 14.29 g (67.4%) of Cl$_3$SiCH$_2$CH$_2$CH$_2$Cl. This example shows that the reaction between Cl$_3$SiH and allyl chloride is promoted very effectively in rate by very low levels (0.33 mol.%) of Et$_3$SiH, with the elimination of external heating.

TABLE XI
PROMOTION OF Cl$_3$SiH AND ALLYL CHLORIDE

| Example | REACTANT A | OLEFIN | PROMOTER | YIELD % | TIME |
|---|---|---|---|---|---|
| Comp. JJ | Cl$_3$SiH | CH$_2$=CHCH$_2$Cl | — | 66.1 | 49 min |
| Comp. KK | Cl$_3$SiH | CH$_2$=CHCH$_2$Cl | Cl$_3$GeH | No Promotion | 7180 min |
| 31 | Cl$_3$SiH | CH$_2$=CHCH$_2$Cl | 10/1 Cl$_3$SiH/Et$_3$SiH | 65.9* | 27 min |
| 32 | Cl$_3$SiH | CH$_2$=CHCH$_2$Cl | 15/1 Cl$_3$SiH/Et$_3$SiH | 63.2** | 18 min |
| 33 | CH$_3$SiH | CH$_2$=CHCH$_2$Cl | 0.33 mol. % Et$_3$SiH | 67.4*** | 24 min |

*With Et$_3$SiH acting as promoter (similar to Example 26 but the ratio of Cl$_3$SiH and Et$_3$SiH is reversed), rate is increased but yield is not increased; here the mixture is added to olefin.
**Here, the order of reaction was reversed (olefin added to mixture) with again higher rates but no effect on yield.

Example 31

Reactant of 10/1 molar mixture of Cl$_3$SiH/Et$_3$SiH with allyl chloride, former added to latter.

In a 50 ml apparatus, there were combined 7.7 g (0.1 mol) of allyl chloride and 0.05 ml of Pt catalyst solution. At 42° C., addition of a mixture of 13.6 g (0.1 mol) of Cl$_3$SiH and 1.2 g (0.01 mol) of Et$_3$SiH was begun. There was an exothermic reaction during addition (27 min) to 77° C. Vacuum distillation yielded 13.98 g (65.9%) of Cl$_3$SiCH$_2$CH$_2$CH$_2$Cl. This example shows that Et$_3$SiH is an effective promoter for the reaction between This Table XI shows that Cl$_3$SiH and allyl chloride can be promoted primarily in their rate by both Et$_3$SiH and EtMe$_2$SiH and slightly in yield by EtMe$_2$SiH. Very small quantities of Et$_3$SiH may be used to promote rate (Example 33), and the order of mixing does not seem to matter (Contrast to Comparative Examples EE and FF and Examples 23–26 as discussed in Table IX.)

Comparative Example OO

Reaction of Et$_3$SiH with 3-chloro-1-butene.

In a 50 ml apparatus, there were combined 4.5 g (0.039 mol) of Et$_3$SiH and 3.5 g (0.039 mol) of 3-chloro-1-butene. Pt catalyst solution (0.01 ml) was added at 22° C., followed by heating up to 77° C. over 70 min. Vacuum distillation yielded 3.46 g (58.9%) of Et$_3$SiCl and 0.61 g (7.6%) of Et$_3$SiCH$_2$CH$_2$CHMeCl. This example demonstrates the low yield of Et$_3$SiCH$_2$CH$_2$CHMeCl from the unpromoted reaction of Et$_3$SiH with 3-chloro-1-butene.

EXAMPLE 34

Reaction of Et$_3$SiH with 3-chloro-1-butene promoted by Cl$_3$SiH.

The reaction of Comparative Example OO was repeated except that 1.0 g (0.007 mol) of Cl$_3$SiH was also added. There was a smooth exothermic reaction to 55° C. in 52 min. with no external heating. Vacuum distillation yielded 2.54 g (22.5%) of Et$_3$SiCl and 11.40 g (73.6%) of Et$_3$SiCH$_2$CH$_2$CHMeCl. This example shows that Cl$_3$SiH is a very effective promoter for the reaction between Et$_3$SiH and 3-chloro-1-butene, increasing both rate and yield, and eliminating external heating.

Comparative Example PP

Reaction of Et$_3$SiH with 4-methyl-1-pentene.

In a 50 ml apparatus, there were combined 6.3 g (0.075 mol) of 4-methyl-1-pentene, 8.7 g (0.075 mol) of Et$_3$SiH, and 0.01 ml of Pt catalyst solution at 22° C. Heat was applied over 2 hr. up to 58° C., with VPC analysis showing 11.0% conversion of reactants to Et$_3$SiCH$_2$CH$_2$CHMe$_2$. This example demonstrates the low rate of the unpromoted reaction between Et$_3$SiH and 4-methyl-1-pentene.

Example 35

Reaction of Et$_3$SiH with 4-methyl-1-pentene promoted by Cl$_3$SiH.

The reaction of Comparative Example PP was repeated except that Cl$_3$SiH (1.0 g, 0.0075 mol) was also added. There was a rapid exothermic reaction from 23° C. to 70° C. in 8 min. VPC analysis at that point showed 29.7% conversion of reactants to Et$_3$SiCH$_2$CH$_2$CH$_2$CHMe$_2$, demonstrating that Cl$_3$SiH is an effective promoter for the reaction of Et$_3$SiH with 4-methyl-1-pentene.

Comparative Example QQ

Reaction of equimolar mixture of Et$_3$SiH/MeSiHCl$_2$ with 4-methyl-1-pentene.

In a 50 ml apparatus, there were combined 8.1 g (0.07 mol) of Et$_3$SiH, 8.1 g (0.07 mol) of MeSiHCl$_2$, and 5.9 g (0.07 mol) of 4-methyl-1-pentene. Pt catalyst solution (0.05 ml) was added at 21° C. Gentle heating caused and exothermic reaction to 55° C. in 38 min. VPC analysis of the complete reaction 90 min. later showed a mixture of MeSiCl$_2$CH$_2$CH$_2$CH$_2$CHMe$_2$/Et$_3$SiCH$_2$CH$_2$CH$_2$CHMe$_2$ in a molar ratio of 3.3/1. This example shows that neither MeSiHCl$_2$ nor Et$_3$SiH is a very effective promoter at the equimolar level for reactions of the other with 4-methyl-1-pentene.

Comparative Example RR

Reaction of equimolar mixture of EtMe$_2$SiH/MeSiHCl$_2$ with 4-methyl-1-pentene.

In a 25 ml apparatus, there were combined 2.6 g (0.023 mol) of MeSiHCl$_2$, 2.0 g (0.023 mol) of EtMe$_2$SiH, and 1.9 g (0.023 mol) of 4-methyl-1-pentene. A few droplets of Pt catalyst solution were added at 22° C. Gentle heating caused an exothermic reaction to 53° C. over 21 min., followed by heating at 50° C. for 130 min. VPC analysis of the complete reaction showed equivalent yields of MeSiCl$_2$CH$_2$CH$_2$CH$_2$CHMe$_2$ and EtMe$_2$SiCH$_2$CH$_2$CH$_2$CHMe$_2$. This example shows that while the promoting effect of EtMe$_2$SiH is nearly equivalent to that of Et$_3$SiH for the reaction of MeSiHCl$_2$ with 4-methyl-1-pentene, its competitive reactivity is significantly higher.

Comparative Example SS and Example 36

Reaction with Et$_3$SiH with 3,3-dimethyl-1-butene promoted by Cl$_3$SiH.

In a 50 ml apparatus, there were combined 11.6 g (0.1 mol) of Et$_3$SiH, 8.4 g (0.01 mol) of 3,3-dimethyl-1-butene, and 0.01 ml Pt catalyst solution at 14° C. Heat was applied up to 86.5° C. over 113 min., when VPC analysis showed 38.4% conversion of reactants to Et$_3$SiCH$_2$CH$_2$CMe$_3$. Reaction was cooled to 60° C. and 0.7 g (5 mol-%) of Cl$_3$SiH added, causing a rapid exothermic reaction to 83° C. in 3 min., and complete conversion of reactants to Et$_3$SiCH$_2$CH$_2$CMe$_3$. This example demonstrates both the low rate of the unpromoted reaction and the effectiveness of Cl$_3$SiH as a promoter for the reaction between Et$_3$SiH and 3,3-dimethyl-1-butene.

EXAMPLE 37

Reaction of equimolar mixture of Cl$_3$SiH/Et$_3$SiH with 3,3-dimethyl-1-butene.

In a 100 ml apparatus, there were combined 11.6 g (0.1 mol) of Et$_3$SiH, 8.4 g (0.1 mol) of 3,3-dimethyl-1-butene, and 13.6 g (0.1 mol) of Cl$_3$SiH. Pt Catalyst solution was added (0.05 ml) at 24° C., causing a rapid exothermic reaction to 57° C. in 4 min. Vacuum distillation yielded 1.82 g (8.3%) of Cl$_3$SiCH$_2$CH$_2$CMe$_3$ and 11.95 g (59.8%) of Et$_3$SiCH$_2$CH$_2$CMe$_3$. This example shows that Cl$_3$SiH is an effective promoter at the equimolar level for the reaction between Et$_3$SiH and 3,3-dimethyl-1-butene.

Comparative Example TT

Reaction of Et$_3$SiH with allyl phenyl ether.

In a 50 ml apparatus, there were combined 10.1 g (0.075 mol) of allyl phenyl ether and 8.7 g (0.075 mol) of Et$_3$SiH. Pt catalyst solution (0.02 ml) was added at 22° C., followed by heating up to 55° C. over 3 hrs. Vacuum stripping left 14.7 g (78.4%) of Et$_3$SiCH$_2$CH$_2$CH$_2$OC$_6$H$_5$.

Example 38

Reaction of Et$_3$SiH with allyl phenyl ether promoted by Cl$_3$SiH.

The reaction of Comparative Example TT was repeated except that 1.4 g (0.01 mol) of Cl$_3$SiH was also added. Gentle heating caused a violent exothermic reaction from 40° C. to 137° C. over 18 min. Vacuum stripping left 19.7 g (78.8%) of Et$_3$SiCH$_2$CH$_2$CH$_2$OC$_6$H$_5$. This example shows that Cl$_3$SiH is an effective promoter for the rate of the reaction between Et$_3$SiH and allyl phenyl ether.

Comparative Example VV

Reaction of Et$_3$SiH with methallyl phenyl ether.

In a 50 ml apparatus, there were combined 5.8 g (0.05 mol) of Et$_3$SiH, 7.4 g (0.04 mol) of methallyl phenyl ether, and 0.02 ml of Pt catalyst solution at 21° C. Heat was applied to 86° C. over 115 min. VPC analysis showed only 21.9% conversion of reactants to Et$_3$SiCH$_2$CHMeCH$_2$OC$_6$H$_5$.

Example 39

Reaction of Et$_3$SiH with methallyl phenyl ether promoted by Cl$_3$SiH.

The reaction of Comparative Example VV was repeated except that 0.7 g (0.005 mol) of Cl$_3$SiH was also added. There was a rapid exothermic reaction from 23° C. to 131° C. in 90 sec. VPC showed 88.4% conversion of reactants to Et$_3$SiCH$_2$CHMeCH$_2$OC$_6$H$_5$, demonstrating that Cl$_3$SiH is a very effective promoter for the reaction of Et$_3$SiH with methallyl phenyl ether. Note that the allyl and methallyl phenyl ethers are chemical models for allyl and methallyl polyalkylene oxide ethers which are articles of commerce.

Comparative Example WW

Reaction of Et$_3$SiH with styrene.

In a 50 ml apparatus, there were combined 8.6 g (0.075 mol) of Et$_3$SiH, 7.8 g (0.075 mol) of styrene, and 0.05 ml Pt catalyst solution at 20° C. There was a slow reaction to 29° C. over 33 min (heat rise due to magnetic stirrer), with VPC analysis showing 1.8% conversion of reactants to Et$_3$SiCH$_2$CH$_2$C$_6$H$_5$.

Example 40

Reaction of Et$_3$SiH with styrene promoted by Cl$_3$SiH.

The reaction of Comparative Example WW was repeated except that 1.0 g (0.0075 mol) of Cl$_3$SiH was also added. There was an exothermic reaction to 39° C. over 38 min., with 24.1% conversion of reactants to Et$_3$SiCHMeC$_6$H$_5$/Et$_3$SiCH$_2$CH$_2$C$_6$H$_5$ (0.59 molar ratio). This example shows that Cl$_3$SiH is an effective promoter for the reaction between Et$_3$SiH and styrene.

Comparative Example XX

Reaction of D$_3$D' with vinyl acetate.

In a 100 ml apparatus, there were combined 30.5 g (0.1 mol) of 92% D$_3$D' and 0.05 ml Pt catalyst solution. Heat was applied to 125° C. and addition of 8.6 g (0.1 mol) of vinyl acetate begun. Continued heating during addition caused an exothermic reaction to 195° C. over 220 min. Vacuum distillation yielded 11.42 g (31.0%) of D$_3$D'CHMeOAc and 4.62 g (12.6%) of D$_3$D'CH$_2$CH$_2$OAc.

EXAMPLE 41

Reaction of D$_3$D' with vinyl acetate promoter by Cl$_3$SiH.

The reaction of Comparative Example XX was repeated except that all reactants were combined at the start and 1.4 g (0.01 mol) of Cl$_3$SiH was also added. Heat was applied to a maximum temp. of 147° C. over 360 min., followed by vacuum distillation, which yielded 5.46 g (14.8%) of D$_3$D'CHMeOAc and 18.78 g (51.0%) of D$_3$D'CH$_2$CH$_2$OAc. This example shows that Cl$_3$SiH is an effective promoter for the reaction between D$_3$D' and vinyl acetate, allowing reaction completion at significantly lower temp. with a much higher yield of the more stable and useful D$_3$D'CH$_2$CH$_2$OAc isomer.

TABLE XII

| | | PROMOTION USING OTHER OLEFINS | | | |
|---|---|---|---|---|---|
| Example | REACTANT A | OLEFIN | PROMOTER | YIELD % | TIME |
| Comp. OO | Et$_3$SiH | 3-chloro-1-butene | — | 7.6 | 70 min |
| 34 | Et$_3$SiH | 3-chloro-1-butene | 18 mol % Cl$_3$SiH | 73.6 | 52 min |
| Comp. PP | Et$_3$SiH | 4-methyl-1-pentene | — | 11.0 | 7120 min |
| 35 | Et$_3$SiH | 4-methyl-1-pentene | 10 mol % Cl$_3$SiH | 29.7 | 8 min |
| Comp. SS | Et$_3$SiH | 3,3-dimethyl-1-butene | — | 38.4 | 113 min |
| 36 | Et$_3$SiH | 3,3-dimethyl-1-butene | 5 mol % Cl$_3$SiH | Comp.* | 3 min |
| 37 | Et$_3$SiH | 3,3-dimethyl-1-butene | EqM. Cl$_3$SiH | 59.8 | 4 min |
| Comp. TT | Et$_3$SiH | allyl phenyl ether | — | 78.4 | >180 min |
| 38 | Et$_3$SiH | allyl phenyl ether | 13 mol % Cl$_3$SiH | 78.8** | 18 min |
| Comp. VV | Et$_3$SiH | methallyl phenylether | — | 21.9 | 115 min |
| 39 | Et$_3$SiH | methallyl phenylether | 10 mol % Cl$_3$SiH | 88.4 | 1½ min |
| Comp. WW | Et$_3$SiH | Styrene | — | 1.8 | 33 min |
| 40 | Et$_3$SiH | Styrene | 10 mol % Cl$_3$SiH | 24.1 | 38 min |
| Comp. XX | D$_3$D' | Vinyl acetate | — | 12.6 | 220 min |
| 41 | D$_3$D' | Vinyl acetate | 10 mol % Cl$_3$SiH | 51 | 360 min |

*Run to Completion

This Table shows, except for the last 2 examples, the effect of Cl$_3$SiH used as a promoter in a reaction between Et$_3$SiH and various other olefins. In each case, this table shows clearly that small amounts (i.e., about 10 mol-%) of Cl$_3$SiH significantly increases either rate or yield of these reactions. The last two examples show the same effect in a reaction between D$_3$D' and vinyl acetate also promoted by Cl$_3$SiH.

EXAMPLE 42

A 250 cc three-necked flask equipped with a 125 cc dropping addition funnel, magnetic stirrer, reflux condenser, thermometer, heating mantle, and nitrogen inlet was charged with 71.5 grams (0.638 moles) allyl acrylate, 0.150 grams phenothiazine inhibitor, 0.150 grams Diphenyl-p-phenylenediamine inhibitor and heated to 50° C. with stirring. When 50° C. was reached, 80 microliters of 10% chloroplatinic acid solution (20 ppm of platinum as based on total reaction charge) was injected into the flask followed by 100 microliters of triethylsilane promoter. A feed of trichlorosilane was introduced slowly to the olefin with continuous stirring over a period of two hours. An exotherm was apparent immediately at the start of the addition. An ice bath was necessary to maintain the reaction mixture between 50°–65° C. throughout the addition. A total of 78.5 grams (0.580 moles) of trichlorosilane was added. Following the complete addition, the reaction mixture was cooled to room temperature and samples for gas chromatographic analysis. Results indicated approximately 70% product of 3-acryloxypropyltrichlorosilane. The identification was verified later by gc/mass spec analysis. Recovery was 145 grams of reaction material.

This example shows the promotional effects of a second silane when the olefin is allyl acrylate. This reaction is important because the generated catalyst allows the reaction to occur at 50°–65° C., thus preventing the polymerization associated with usage of unstable acrylates at higher temperatures. While some product would form without promotion, it is uncertain when reaction initiation would occur. Thus the effective yield increase is great compared to the unpromoted reaction.

I claim:

1. In the process of preparing compounds containing silicon-carbon bonds by the hydrosilation reaction of a hydrosilyl reactant with an olefinic reactant in the presence of a soluble platinum catalyst, the improvement which comprises operating the process at a temperature below 150° C. and employing, as a reaction promoter, a hydrosilyl compound whereby said hydrosilyl reactant has a composition different from the composition of said promoter and whereby said promoter provides (i) a 20% increase in the amount of silicon-carbon compounds, or (ii) a 20% increase in reaction rate relative to an unpromoted reaction.

2. The process according to claim 1 wherein said hydrosilyl reactant has the general formula $R_3SiH$ where each R is a monovalent hydrocarbon group, aliphatic having 1–10 carbon atoms or aromatic having 6–20 carbon atoms, free of terminal unsaturation, where said R group is unsubstituted or substituted with functional groups, with the proviso that when said hydrosilyl reactant is substituted to functional groups, said functional groups do not interfere in the promotion of the hydrosilation reaction.

3. The process of claim 2 wherein R is selected from the group consisting of alkyl, aryl, alkoxy, acyloxy, and carbamoyloxy.

4. The process according to claim 1 wherein said hydrosilyl reactant has the general formula $R_3SiH$ where R is halogen or siloxy.

5. The process of claim 2 wherein the hydrosilyl reactant has a substituted functional group selected from the group consisting of halogen, cyano, carboalkoxy, ether, and thioether.

6. The process of claim 2 wherein the hydrosilyl reactant has at least two R groups to form a heterocyclic ring including the silicon.

7. The process of claim 6 wherein the hydrosilyl reactant is

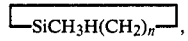

where n=3–6.

8. The process according to claim 1 wherein the hydrosilyl promoter has the general formula $R_3SiH$ where each R represents a monovalent hydrocarbon group, aliphatic having 1–10 carbon atoms or aromatic having 6–20 carbon atoms free of terminal unsaturation, where said R group is unsubstituted or substituted with functional groups, with the proviso that when said hydrosilyl promoter is substituted to form functional groups, said functional groups do not interfere in the promotion of the hydrosilation reaction.

9. The process of claim 8 wherein R is selected from the group consisting of alkyl, aryl, alkoxy, acyloxy and carbamoyloxy.

10. The process according to claim 1 wherein the hydrosilyl promoter has the general formula $R_3SiH$ where R represents halogen or siloxy.

11. The process of claim 8 wherein the hydrosilyl promoter has a substituted functional group selected from the group consisting of halogen, cyano, carboalkoxy, ether and thioether.

12. The process according to claim 1 wherein said promoter is selected from the group consisting of $Cl_3SiH$, $MeSiHCl_2$, $Me_2SiHCl$, $Et_3SiH$, $F_3SiH$ and $Br_3SiH$.

13. The process according to claim 1 where the promoter is $Cl_3SiH$ and the hydrosilyl reactant is $(CH_3CH_2)_3SiH$.

14. The process according to claim 1 where the promoter is $(CH_3CH_2)_3SiH$ and the hydrosilyl reactant is $Cl_3SiH$.

15. The process according to claim 1 where the promoter is $(CH_3CH_2)_3SiH$ and the hydrosilyl reactant is $(CH_3O)_3SiH$.

16. The process according to claim 1 wherein the olefinic reactant has the general formula $CH_2{=}C{<}$.

17. The process of claim 16 wherein the olefin is selected from the group consisting of allyl and methallyl compounds, vinyl compounds, terminal alkenes, including halides, ethers, esters and nitriles, with the proviso that when the olefinic reactant is substituted to functional groups, said functional groups do not interfere with the hydrosilation reaction.

18. The process according to claim 16 wherein the olefinic reactant is an allyl or methallyl polyalkylene oxide ether.

19. The process according to claim 16 wherein the olefinic reactant is allyl acrylate.

20. The process according to claim 1 wherein said reaction is run at sub-ambient temperatures.

21. The process of claim 1 wherein said soluble platinum compound is chosen from the group consisting of solutions of $H_2PtCl_6$, in hydrated or unhydrated form, solutions of $PtCl_4$ or $PtCl_2$ and solutions of ethylene bis (platinum chloride).

22. The process of claim 1 wherein said reaction promoter is used at 0.0001–2.0 molar amounts relative to the hydrosilyl reactant, and said reactant containing carbon-carbon olefinic unsaturation is used at 0.1–2.0 molar amounts relative to the silicon-bonded hydrogen reactant.

* * * * *